United States Patent
Heinecke et al.

(10) Patent No.: US 7,749,729 B2
(45) Date of Patent: Jul. 6, 2010

(54) METHODS FOR ASSESSING THE RISK FOR DEVELOPMENT OF CARDIOVASCULAR DISEASE

(75) Inventors: Jay W. Heinecke, Seattle, WA (US); John F. Oram, Seattle, WA (US)

(73) Assignee: University of Washington, Seattle, WA (US)

( * ) Notice: Subject to any disclaimer, the term of this patent is extended or adjusted under 35 U.S.C. 154(b) by 291 days.

(21) Appl. No.: 11/572,308

(22) PCT Filed: Jul. 19, 2005

(86) PCT No.: PCT/US2005/025551

§ 371 (c)(1),
(2), (4) Date: Jun. 4, 2007

(87) PCT Pub. No.: WO2006/014628

PCT Pub. Date: Feb. 9, 2006

(65) Prior Publication Data

US 2008/0261250 A1 Oct. 23, 2008

Related U.S. Application Data

(60) Provisional application No. 60/714,517, filed on Jul. 19, 2004.

(51) Int. Cl.
*G01N 33/53* (2006.01)
(52) U.S. Cl. ...................................................... 435/41
(58) Field of Classification Search ........................ None
See application file for complete search history.

(56) References Cited

FOREIGN PATENT DOCUMENTS

WO 01/38395 A1 5/2001
WO 2005/055810 A2 6/2005

OTHER PUBLICATIONS

Nakajima et al. Biochem Biophy Res Comm 1995 vol. 217, p. 407-411.*
Bergt et al. (Free Radical Biology & Medicine 2003 S101 item 312).*
Nakajima et al. Annals Clinical Biochem 2000 vol. 37, p. 179-186.*
Aviram, M., "Does Paraoxonase Play a Role in Susceptibility to Cardiovascular Disease?" Molecular Medicine Today 5(9):381-386, Sep. 1999.
Bergt, C.F., et al., "Hypochlorous Acid Generated by the Myeloperoxidase System of Activated Phagocytes Promotes Extensive Oxidative Fragmentation of Apolipoprotein A-I in Human High Density Lipoprotein: Implications for Atherogenesis," Free Radical Biology and Medicine 29(10 Suppl. 1):S80, 2000.

(Continued)

*Primary Examiner*—Jacob Cheu
(74) *Attorney, Agent, or Firm*—Christensen O'Connor Johnson Kindness PLLC

(57) ABSTRACT

The present invention relates to diagnostic tests, methods and kits that are useful to assess a subject's risk of developing a pathologic condition related in part to the presence of HDL oxidation product. Measuring the quantity of one or more HDL oxidation products present in the blood is useful in evaluating risk for developing or evaluating the severity of a disease or evaluating response to treatment for such a disease as, for instance, cardiovascular disease.

24 Claims, 20 Drawing Sheets

OTHER PUBLICATIONS

Bergt, C., et al., "Lysine Residues Direct the Chlorination of Tyrosines in YXXK Motifs of Apolipoprotein A-I When Hypochlorous Acid Oxidizes High Density Lipoprotein," The Journal of Biological Chemistry 279(9):7856-7866, Feb. 27, 2004.

Bergt, C., et al., "Tyrosine Chlorination in Apo A-I is Directed By Lysine Residues When Hypochlorous Acid Oxidizes HDL," Free Radical Biology and Medicine 35(Suppl. 1):S101, Nov. 24, 2003.

Martin-Nizard, F., et al., "Oxidized High-Density Lipoproteins Modulate Endothelin Secretion by Adult Bovine Aortic Endothelial Cells," Journal of Cardiovascular Risk 2(3):263-267, Jun. 1995.

Matsunaga, T., et al., "Glycated High-Density Lipoprotein Induces Apoptosis of Endothelial Cells via a Mitochondrial Dysfunction," Biochemical and Biophysical Research Communications 287(3):714-720, Sep. 2001.

Matsunaga, T., et al., "Modulation of Reactive Oxygen Species in Endothelial Cells by Peroxynitrite-Treated Lipoproteins," Journal of Biochemistry 130(2):285-293, Aug. 2001.

* cited by examiner

METHODS FOR ASSESSING THE RISK FOR DEVELOPMENT OF CARDIOVASCULAR DISEASE

CROSS-REFERENCE TO RELATED APPLICATIONS

This application is the National Phase of International Application No. PCT/US2005/025551 filed Jul. 19, 2005, which claims the benefit of U.S. Provisional Patent Application No. 60/714,517, filed Jul. 19, 2004, the disclosures of which are incorporated herein by reference in their entirety.

GOVERNMENTAL RIGHTS

This invention was made through funding by the National Institutes of Health (NIH Grant AG 19309). The United States government has certain rights in this invention.

FIELD OF THE INVENTION

The invention relates to diagnostic methods for assessing the risk of a subject for development of a pathological condition associated with high levels of oxidative stress induced compounds, in particular, cardiovascular disease. In addition, methods are described for monitoring the effectiveness of therapy in a subject, and for establishing a prognosis in a subject undergoing treatment for a condition such as a cardiac condition using specific markers of oxidative stress as indicators of disease progression or inhibition thereof.

BACKGROUND OF THE INVENTION

Cardiovascular disease (CVD) is a general term used to classify numerous conditions that affect the heart, heart valves, blood, and vasculature of the body. Cardiovascular diseases include coronary artery disease, angina pectoris, myocardial infarction, atherosclerosis, congestive heart failure, hypertension, cerebrovascular disease, stroke, transient ischemic attacks, cardiomyopathy, arrhythmias, aortic stenosis, and aneurysm. Signs and symptoms of cardiovascular disease include chest, neck, or arm pain, palpitations (irregular heart beat), dyspnea (shortness of breath), syncope (fainting), fatigue, cyanosis (bluish coloration of the lips and nails), and claudication (leg pain).

Cardiovascular disease remains the number one killer of people in the United States today. The diagnosis of CVD is made by assessing a patient's clinical symptoms, by running laboratory tests to determine levels of certain enzymes, as well as by coronary angiography, electrocardiogram, and an exercise stress test (treadmill).

There are many risk factors that may contribute to the development of CVD. Certain of these risk factors are modifiable. These include cigarette smoking, high LDL cholesterol, low HDL cholesterol, diabetes, hypertension, and physical inactivity. Other contributing risk factors include obesity, diet, and alcohol consumption. Some risk factors are not capable of being modified and these include age, sex, race, and family history.

The optimal treatment for CVD is prevention and modification of risk factors. If the disease has progressed beyond prevention and modification, surgical intervention including percutaneous transluminal coronary angioplasty (PTCA), coronary bypass, and coronary stents may be performed and or implanted.

While the risk factors for CVD are used by physicians in risk prediction matrices in an attempt to target those individuals who are at highest risk for development of CVD, thereby allowing these individuals to modify their lifestyle to lower their risk profile to the extent possible, these algorithms are still limited in their predictability. Accordingly, there is a need for expanding these algorithms to take into account other factors that should be included in a patient's risk profile for development of CVD.

It is generally recognized that many disease processes are associated with the presence of elevated levels of oxidative stress induced compounds, such as free radicals and reactive oxygen species (ROS) and reactive nitrogen species (RNS). These include superoxide, hydrogen peroxide, singlet oxygen, peroxynitrite, hydroxyl radicals, hypochlorous acid (and other hypohalous acids) and nitric oxide.

For example, in the eye, cataract, macular degeneration and degenerative retinal damage are attributed to ROS. Other organs and their ROS-related diseases include: lung cancer induced by tobacco combustion products and asbestos; accelerated aging and its manifestations, including skin damage and scleroderma; atherosclerosis; ischemia and reperfusion injury, diseases of the nervous system such as Parkinson disease, Alzheimer disease, muscular dystrophy, multiple sclerosis; lung diseases including emphysema and bronchopulmonary dysphasia; iron overload diseases such as hemochromatosis and thalassemia; pancreatitis; diabetes; renal diseases including autoimmune nephrotic syndrome and heavy metal-induced nephrotoxicity; and radiation injuries. Diseases of aging and chronic emotional stress also appear to be associated with a drop in glutathione levels, which allows ROS to remain active.

However, while there has been an association of these disease states with high levels of oxidative stress induced compounds, the reliance of these compounds for use as a marker of risk for development of these diseases has not been demonstrated. On the other hand, there is current evidence in animal studies that oxidation of LDL occurs in vivo, and the results suggest that this may lead to the formation and build up of atherosclerotic plaques.

A wealth of evidence suggests that LDL must be oxidatively modified to damage the artery wall (Heinecke, (1998) *Atheroscler.* 141, 1-15). One pathway for LDL oxidation in humans has been described (Daugherty et al. (1994) *Journal of Clinical Investigation* 94, 437-444). It involves hypochlorous acid and other reactive intermediates generated by myeloperoxidase, a heme protein secreted by phagocytes. High concentrations of enzymatically active myeloperoxidase have been found in human vascular lesions (Sugiyama et al., (2001) *Am J Pathol* 158, 879-891.), and the enzyme's characteristic protein and lipid oxidation products have been detected in LDL isolated from atherosclerotic tissue (Hazen, et al., (1997) *J. Clin. Invest.* 99, 2075-2081; Heller et al., (2000) *J. Biol Chem* 275, 9957-9962; Leeuwenburgh et al., (1997) *J. Biol. Chem.* 272, 3520-3526).

Another oxidative pathway involves nitric oxide (nitrogen monoxide; NO), which is generated by vascular wall cells (Moncada, et al., (1991) *Pharmacological Reviews* 43, 109-142). NO is a relatively stable free radical that is unable to oxidize LDL directly under physiological conditions (Beckman, et al. (1996) *Am J Physiol* 271, C1424-1437; Ischiropoulos, (2003) *Biochem Biophys Res Commun* 305, 776-783). However, it reacts rapidly with superoxide to form peroxynitrite (ONOO⁻) (Beckman et al., (1990) *Proceedings of the National Academy of Sciences of the United States of America* 87, 1620-1624), a reactive nitrogen species that promotes peroxidation of the lipid moiety of LDL in vitro (Graham et al., (1993) *FEBS Letters* 330, 181-185). Proteins also appear vulnerable to ONOO⁻ because the oxidant reacts in vitro with tyrosine residues to yield the stable product 3-nitrotyrosine (Beckman, et al, (1994) *Methods in Enzymology* 233, 229-240). LDL isolated from human atherosclerotic lesions contains much higher levels of 3-nitrotyrosine than does circulating LDL, as monitored by isotope dilution gas chromatography-mass spectrometry (GC/MS), a sensitive and specific method (Leeuwenburgh et al., (1997) *Journal of Biological Chemistry* 272, 1433-1436). These observations indicate that reactive nitrogen species oxidize LDL in the human artery wall.

Cultured endothelial cells, macrophages, and smooth muscle cells, all components of the atherosclerotic lesion, generate superoxide anion. Moreover, elevated levels of nitrated plasma proteins associate with an increased risk of coronary artery disease, suggesting that oxidants derived from NO modify circulating proteins or proteins that find their way into the bloodstream (Shishehbor et al., (2003) *Jama* 289, 1675-1680). Fibrinogen is one target for nitration in plasma. Also, exposing fibrinogen to nitrating oxidants in vitro accelerates clot formation (Vadseth et al., (2004) *J Biol Chem* 279, 8820-8826).

NO can also autoxidize to nitrite ($NO_2^-$), and plasma levels of $NO_2^-$ rise markedly during acute and chronic inflammation (Farrell et al., (1992) *Ann Rheum Dis* 51, 1219-1222). Because $NO_2^-$ is a substrate for myeloperoxidase and other peroxidases, it may also be used to nitrate tyrosine in vivo (Klebanoff, (1993) *Free Radio Biol Med* 14, 351-360; Chance, (1952) *Arch Biochem Biophys* 41, 425-431). Indeed, myeloperoxidase uses hydrogen peroxide ($H_2O_2$) and $NO_2^-$ to generate reactive nitrogen species that nitrate free and protein-bound tyrosine residues and promote lipid peroxidation of LDL in vitro (Eiserich et al., (1996) *Journal of Biological Chemistry* 271, 19199-19208; Eiserich et al., (1998) *Nature* 391, 393-397; Byun et al., (1999) *FEBS Letters* 455, 243-246; Podrez et al., (1999) *J Clin Invest* 103, 1547-1560). These reactions might be physiologically relevant because tyrosine nitration is markedly impaired in a model of peritoneal inflammation in myeloperoxidase-deficient mice by a reaction pathway that appears to require $NO_2^-$ or other intermediates derived from NO (Gaut et al., (2002) *J Clin Invest* 109, 1311-1319). In human atherosclerotic lesions, most cell-associated myeloperoxidase is found in and around macrophages (Daugherty et al., (1994) *Journal of Clinical Investigation* 94, 437-444). However, the enzyme has also been detected in endothelial cells (Baldus et al., (2001) *J Clin Invest* 108, 1759-1770), raising the possibility that reactive intermediates produced by peroxidases might generate the epitopes on macrophages and endothelial cells that are recognized by antibodies to 3-nitrotyrosine.

High density lipoprotein (HDL) protects the artery wall against the development of atherosclerosis (reviewed in Miller et al., O.D. 1977. *Lancet* 1:965-968; Keys, A. 1980. *Lancet* 2:603-606). This atheroprotective effect is attributed mainly to HDL's ability to mobilize excess cholesterol from arterial macrophages. Cell culture experiments have uncovered several mechanisms that enable components of HDL to remove cellular cholesterol (Oram, et al., 1996. *J Lipid Res* 37:2473-2491; Rothblat et al., 1999. *J Lipid Res* 40:781-796). For example, phospholipids in HDL absorb cholesterol that diffuses from the plasma membrane, a passive process facilitated by the interaction of HDL particles with scavenger receptor B1. In contrast, HDL apolipoproteins remove cellular cholesterol and phospholipids by a cholesterol-inducible active transport process mediated by a cell membrane protein called ATP-binding cassette transporter A1 (ABCA1) (5-8).

The most abundant apolipoprotein in HDL is apolipoprotein (apo) A-I, which accounts for ~70% of HDL's total protein content. Lipid-poor apo A-I promotes efflux of cellular cholesterol and phospholipids exclusively by the ABCA1 pathway (Brooks-Wilson et al., 1999. *Nat Genet.* 22:336-345; Bodzioch et al., 1999. *Nat Genet.* 22:347-351; Rust et al., 1999. *Nat Genet.* 22:352-355; Lawn et al., 1999. *J Clin Invest* 104:R25-31). This process appears to involve the amphipathic α-helical domains in apo A-I (Oram, J. F. 2003. *Arterioscler Thromb Vasc Biol* 23:720-727). Studies of synthetic peptides and deletion mutants of apo A-I suggest that the terminal helices of apo A-I penetrate into the phospholipid bilayer of membranes, promoting cooperative interactions between other α-helical segments and lipids to create an apolipoprotein/lipid structure that dissociates from membranes (Gillotte et al, 1999. *J Biol Chem* 274:2021-2028). This atheroprotective process is inhibited by oxidative damage, which is implicated in the pathogenesis of atherosclerosis (Diaz et al., Jr. 1997. *N Engl J Med* 337:408-416.).

Myeloperoxidase uses hydrogen peroxide to convert chloride to hypochlorous acid (HOCl), which reacts with tyrosine to form 3-chlorotyrosine (Heinecke, (1998) *Atheroscler.* 141, 1-15). At plasma concentrations of chloride ion, myeloperoxidase is the only human enzyme known to produce HOCl. Chlorination of the phenolic ring of tyrosine may have physiological relevance because elevated levels of 3-chlorotyrosine and other products characteristic of myeloperoxidase have been detected in LDL isolated from human atherosclerotic lesions (Hazen et al., 1997. *J Clin Invest* 99:2075-2081; Leeuwenburgh et al., 1997. *J Biol Chem* 272:3520-3526; Heller et al., 2000. *J Biol Chem* 275:9957-9962). Moreover, methionine and phenylalanine residues in apo A-I are oxidized by reactive intermediates (Panzenboeck et al., 2000. *J Biol Chem* 275:19536-19544; Bergt et al., 2000. *Biochem J* 346 Pt 2:345-354; Garner et al., 1998. *J Biol Chem* 273:6080-6087), and tyrosine residues are converted to o,o'-dityrosine by tyrosyl radical (Francis et al., 1993. *Proc Natl Acad Sci USA* 90:6631-6635). HOCl selectively targets tyrosine residues in apo A-I that are suitably juxtaposed to primary amino groups in proteins (Bergt et al., 2004. *J Biol Chem* 279:7856-7866). This mechanism might enable phagocytes to efficiently damage proteins during inflammation.

There is still a need for diagnostic tests to aid in the characterization of subjects at risk for developing diseases characterized in part by high levels of oxidative stress-induced compounds such as HDL oxidation products, in particular, cardiovascular disease. Furthermore, there is a need to establish whether a specific therapy is having the appropriate effect in individuals suffering from such conditions. Thus, prognostic markers or indicators to monitor the effects of such therapy are also needed.

SUMMARY OF THE INVENTION

In its broadest aspect, the invention relates to methods and kits for assessing a pathological condition associated in part with abnormal levels of HDL oxidation products. In a more particular aspect, the present invention provides a means for determining whether a subject is at risk for developing cardiovascular disease or for assessing a subject's risk of having progressive cardiovascular disease as may be manifested, for instance by clinical sequelae, including myocardial infarction, stroke, and peripheral vascular disease, renal disease, or renal failure. In addition, the invention provides methods for evaluating the effectiveness of therapy with an agent useful in preventing or treating cardiovascular disease and for establishing a prognosis in a patient suffering from a cardiovascular condition, during or after treatment with agents effective in treating such conditions. The present invention takes advantage of the discovery that patients having coronary artery disease have significantly greater levels of oxidized high density lipoprotein (HDL) products than patients without coronary artery disease. In particular, the invention provides for measuring such oxidized high density lipoprotein (HDL) products as a means of assessing a pathological condition such as a cardiovascular disease.

Accordingly, a first aspect of the invention provides a method for assessing a pathological condition in which abnormal levels of oxidized high density lipoprotein (HDL) products are associated with the pathological condition. Such assessing may include diagnosing the pathological condition, determining the risk for developing the pathological condition, determining the severity of the pathological condition or monitoring the efficacy of a therapy for the pathological condition.

In a second aspect, the invention provides a method for assessing a subject's risk for developing a cardiovascular disease. An individual who demonstrates an increase in oxidized high density lipoprotein (HDL) products, as compared to a predetermined normal reference range, is at greater risk for developing cardiovascular disease or for having cardiovascular disease progress as may be evidenced for instance by a heart attack, stroke, peripheral vascular disease or renal disease than individuals whose oxidized high density lipoprotein (HDL) product levels are within a normal reference range. The invention contemplates a risk matrix whereby correlating an individual's measured oxidized high density lipoprotein (HDL) product levels with the matrix may be used to predict the individual's risk for developing or having cardiovascular disease, or for having progressive cardiovascular disease as may be manifested, for instance by heart attack.

A third aspect of the invention provides a method for assessing efficacy of a therapy useful for treating cardiovascular disease. The method comprises collecting a series of biological samples from a subject suffering from cardiovascular disease, the samples may be obtained before initiation of therapy and/or at one or more times during administration of therapy. The level of oxidized high density lipoprotein (HDL) products is quantified using the methods as described herein. Oxidized high density lipoprotein (HDL) products and a normalization of oxidized high density lipoprotein (HDL) products correlates with effectiveness of therapy.

A fourth aspect of the invention provides a method for monitoring cardiovascular function in a patient, or for establishing a prognosis in a patient suffering from a cardiovascular condition using the diagnostic tests and methods described herein. In addition to establishing the quantity of oxidized high density lipoprotein (HDL) products, the levels of such products may be compared to at least one cardiac function test, either concurrently or at a different time. The values of oxidized high density lipoprotein (HDL) products may be correlated to a favorable cardiac function test or to an unfavorable cardiac function test.

A fifth aspect of the invention provides a method for monitoring oxidative stress. Oxidative stress has been implicated in the pathogenesis of diseases including atherosclerosis, acute lung injury, arthritis, and carcinogenesis as well as the aging process itself. Prior to the present invention there were no well accepted markers of oxidative stress in humans, nor has it been established that proposed "antioxidants" lower or prevent oxidative stress in human disease or aging. The values of oxidized HDL may be associated with the overall level of oxidative stress. Acute or chronic forms of oxidative stress in disorders like acute lung injury or rheumatoid arthritis may result in increased levels of oxidized HDL. Moreover, the ability of compounds with proposed antioxidant activities such as vitamin E to actually lower oxidative stress in humans may be associated with the levels of oxidized HDL.

In a particular embodiment, the methods according to the invention comprise the following steps:

a) obtaining a biological sample from an individual;

b) measuring the level of one or more oxidized high density lipoprotein (HDL) products in the biological sample;

c) comparing the level of one or more oxidized high density lipoprotein (HDL) products with a range of predetermined values for oxidized high density lipoprotein (HDL) products wherein the level of one or more oxidized high density lipoprotein (HDL) products correlates with the presence of one or more risk factors for the pathological condition.

Particularly, an increase in the level of one or more oxidized high density lipoprotein (HDL) products to a value above the normal range correlates with the presence of, or the pending onset of a pathological condition. The biological sample may be whole blood or a derivative thereof, including but not limited to, whole blood cells, whole blood cell lysates, erythrocytes, plasma, serum, white blood cells, including leukocytes, neutrophils and monocytes. In other embodiments, the biological sample may be other tissues or fluids, including but not limited to cerebral spinal fluid (for neurological diseases), bronchoalevolar lavage fluid (for lung disease), joint fluid (for arthritis), and urine (for systemic disorders and disorders of the kidney, ureters and bladder). In yet other embodiments, the biological sample may be a specific component of HDL itself, including but not limited to apolipoprotein apo A-I, apo A-II, apo A-V, apo CI, CII or CIII, SAA, paraoxonase, platelet activating factor hydrolase (PAF), or lipids or vitamins associated with HDL. In preferred embodiments, the pathological condition is cardiovascular disease. Cardiovascular disease includes, but is not limited to, atherosclerosis, coronary heart disease, ischemic heart disease, myocardial infarction, angina pectoris, peripheral vascular disease, cerebrovascular disease, stroke, renal disease, and other conditions related to or resulting from an ischemic event.

The present invention encompasses a risk matrix that may be developed correlating values of oxidized high density lipoprotein (HDL) products with risk for developing or progressing or for the severity of cardiovascular disease or other disorders associated with oxidative stress and sequelae of the same.

The oxidized high density lipoprotein (HDL) products that are quantified may be any oxidation product indicative of cell injury such as those that react with peroxynitrite or hypochlorous acid. These oxidized products are the product of oxidation of one or more amino acids such as tyrosine, of the lipid portions of the HDL or of molecules in conjuction with the HDL complex such as a vitamin. Preferred oxidized high density lipoprotein (HDL) products may include a product of apo A1 and may be selected from the group consisting of 3-nitrotyrosine, 3,5-dinitrotyrosine, 3-chlorotyrosine, nitrophenyl alanine, chlorophenyl alanine, o',o'-dityrosine, ortho-tyrosine, meta-tyrosine, WG-4 (cross-linked tryptophan-glycine), oxo-tryptophan, p-hydroxyphenylacetic acid (pHA), and pHA adducts of lysine or lipids.

A sixth aspect of the invention provides a kit for measuring the levels of oxidized high density lipoprotein (HDL) products. Such a kit may comprise one or more of a buffer, an antibody, a chemical reagent and a positive control for one or more oxidized high density lipoprotein (HDL) products.

DETAILED DESCRIPTION

Figure 1:
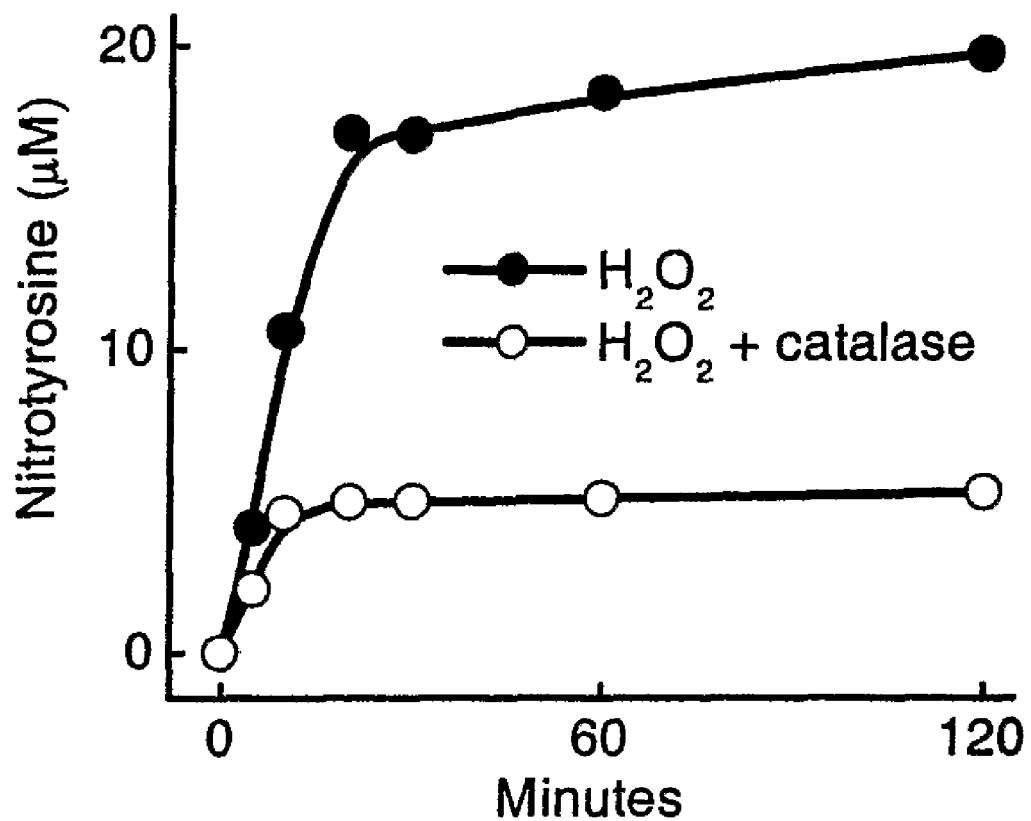
FIG. 1 describes nitration of HDL by the myeloperoxidase-$H_2O_2$-nitrite system. (A,C) HDL (1 mg/ml protein) was incubated for 60 min or the indicated time at 37° C. in phosphate buffer (20 mM sodium phosphate, pH 7.4, 100 μM DTPA) supplemented with 50 nM myeloperoxidase, 250 μM $H_2O_2$ and 500 μM $NO_2^-$. Where indicated, the concentrations of (B) $NO_2^-$ were varied. 3-Nitrotyrosine formation was monitored spectroscopically following alkalinization of the reaction mixture.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the particular methods and materials are now described. All publications mentioned herein are incorporated herein by reference.

DEFINITIONS

The terms used herein have the meanings recognized and known to those of skill in the art; however, for convenience and completeness, particular terms and their meanings are set forth below.

"Treatment" refers to the administration of a drug or the performance of procedures with respect to a subject, for either prophylaxis (prevention) or to cure the infirmity or malady in the instance where the subject is afflicted.

As used herein, "assessing" refers to determining whether an individual is at risk or susceptible to developing a disease or pathological condition caused in part by abnormal levels of one or more oxidized high density lipoprotein (HDL) product. The condition may be any in which there exists a higher than normal level of oxidative stress compounds, such as those described in the present invention. However, one particular condition for which a correlation has been made is cardiovascular disease. A determination may be made based on the particular disease and symptoms associated with the disease, and whether or not the cause of the disease or condition may be attributed, at least in part, to high levels of oxidation of cells, tissues, proteins or other molecular or chemical entities which are candidates for damage caused by oxidative stress, as evidenced by high levels of one or more oxidized high density lipoprotein (HDL) products.

By "individual" or "patient" or "subject" is meant a human or non-human mammal that may benefit from the diagnostic tests or methods described in the present application, for example, an individual at risk for developing or having a cardiovascular disease or one at risk for having a heart attack. Alternatively, other individuals may be predisposed to diseases or conditions other than cardiovascular disease, caused by high levels of oxidative stress. Accordingly, the individual may be treated prophylactically with agents appropriate for the specific disease. For example, in the case of cardiovascular disease, the individual may be required to alter their life style such that a strict regimen of diet and exercise may be necessary to stabilize their condition.

"Surrogate biomarker" or "biomarker" or "marker" as used herein, refers to a highly specific molecule, the existence and levels of which are causally connected to a complex biological process, and reliably captures the state of the process. Furthermore, a surrogate biomarker, or marker, to be of practical importance, must be present in samples that can be obtained from individuals without endangering their physical integrity or well-being, preferentially from biological fluids such as blood, plasma, urine, saliva, CSF or tears. While the markers of oxidative damage include the products of oxidative stress, such as increased lipid peroxides, decreased glutathione, or dityrosine, nitrotyrosine, dinitrotyrosine, 3-chlorotyrosine, nitrophenyl alanine, chlorophenyl alanine, and the levels of these biomarkers should reflect the degree of oxidative stress in the body as a result of certain diseases or conditions, it is to be understood that measuring the levels of enzymes responsible for generation of these products is also useful for assessing the risk factors for development of certain diseases, as described herein. Thus, the oxidized high density lipoprotein (HDL) products can also be considered as markers of the disease process, or risk prognosticators, especially in cardiovascular disease, since there is an elevation in oxidized high density lipoprotein (HDL) products in patients suffering from CVD, or at risk for developing CVD. Furthermore, the presence of these biomarkers should reflect the need for either prophylactic therapy, or for a need for possible future therapy with appropriate cardiovascular drugs. Alternatively, when the levels of these two markers fall outside of the normal range, a patient may be put on a regimen of diet and exercise until the level of markers normalizes. The normalization of these markers as well as normalization of the levels of other tests commonly used to diagnose CVD should also reflect the efficiency of therapy if a patient is undergoing such therapy.

By "efficacy" is meant whether the treatment results in a desired outcome. For example, in the case of treating a patient having high levels of oxidized high density lipoprotein (HDL) products, an increase in the amount of atherosclerotic plaque which ultimately may lead to progressive cardiovascular disease correlates with an increased level of the subject HDL oxidation products. A desired outcome is therefore reduction in the levels of HDL oxidation products.

The "reference range", as used herein, can be determined by one skilled in the art using the methods described herein by a laboratory that can establish a range of levels of oxidized high density lipoprotein (HDL) that are characteristic for either an individual free of, or not susceptible to, a pathological condition, such as a cardiovascular disease, or who are not predisposed for having progressive cardiovascular disease or further sequelae therefrom, and establishing the range of oxidized high density lipoprotein (HDL) in a subject prone to such conditions. This "reference range" may be used in the methods of the present invention for comparative purposes when testing a patient for the presence of or the susceptibility to acquiring such conditions as outlined herein. Based on this comparison, a conclusion may be drawn as to whether a pathological condition, such as a cardiovascular disease, is present in the subject being tested. Those skilled in the art will appreciate how to establish a cut-off value suitable for differentiating subjects suffering from such conditions from subjects not suffering from such conditions.

"Vulnerable plaque" is a type of fatty buildup in an artery thought to be caused by inflammation. The plaque is covered by a thin, fibrous cap that upon rupture may lead to the formation of a blood clot and, ultimately, occlusion of the artery. Plaque rupture most often occurs in smaller arteries, such as the coronary arteries, which supply blood to the heart muscle. The occlusion of a coronary artery can lead to a heart attack. Even moderately occluded arteries with areas of vulnerable plaque are also likely to lead to a heart attack.

General Description

The present invention relates to diagnostic tests and methods to better identify those subjects having, or at risk for developing, a pathological condition associated with abnormal levels of one or more oxidized high density lipoprotein (HDL) products, in particular, cardiovascular disease.

Oxidative stress has been implicated in a number of pathological disease processes, including atherosclerosis (Makela R. et al. (2003) *Lab Invest* 83(7):919-25). Oxidative stress may be defined as an imbalance between the production and degradation of reactive oxygen species such as superoxide anion, hydrogen peroxide, lipid peroxides, and peroxynitrite. Enzymatic degradation of these reactive oxygen species is achieved primarily by the enzymes glutathione peroxidase, superoxide dismutase and catalase (Forsberg et al. (2001) *Arch Biochem Biophys* 389: 84-93).

The glutathione/glutathione peroxidase system is one of the primary antioxidant defense systems in mammals. Glutathione peroxidase 1 is the key antioxidant enzyme in most cells, and this enzyme uses glutathione to reduce hydrogen peroxide to water and lipid peroxides to their respective alcohols ((Flohe, L. (1988), *Basic Life Sci* 57: 1825-35). Mice having a deficiency in this enzyme demonstrate abnormal vascular and cardiac function and structure (Forgione, M. et al. (2002), 106:1154-8). More recent studies in humans by Blankenberg et al. have shown that a low level of activity of this enzyme (GPX) is associated with an increased risk of cardiovascular events (Blankenberg, S, et al. (2003), N. England J. Med. 349: 1605-1613).

Currently, several of the known risk factors for cardiovascular disease are used by physicians in risk prediction algorithms in an attempt to target those individuals who are at highest risk for development of CVD. If an individual presents with a high-risk profile, the individual may be placed on appropriate therapy to address those factors that can be controlled or modified. Other risk factors associated with CVD may be addressed by simple changes in lifestyle thereby allowing these individuals to modify certain factors to lower their risk profile, e.g., changes in diet or exercise. There is a need for expanding such algorithms to take into account other factors that should be included in a patient's risk profile for development of CVD.

Accordingly, the present invention provides a multidimensional and comprehensive method for assessing an individual's risk for developing diseases associated with high levels of oxidative stress-induced compounds, such as CVD. Previous tests for measuring an individual's level of oxidative stress have relied primarily on the measurement of one primary marker of oxidative stress, such as lipid peroxides. The present invention provides for the quantitation of oxidized high density lipoprotein (HDL) products. The present invention will thus provide for the interrelationship between disease risk or state and oxidized high density lipoprotein (HDL) products.

It is a further object of the present invention to be able to measure the efficacy of therapy once an individual has started therapy with agents known to those skilled in the art. The results, when combined with other risk factors for the specific disease, such as, but not limited to CVD, aid in assessing an individual's potential susceptibility for these diseases, which result in part from an increase in oxidized high density lipoprotein (HDL) products.

Establishing a Range of Oxidized High Density Lipoprotein (HDL) Products Values

The "reference range" for oxidized high density lipoprotein (HDL) products, as used herein, can be determined by one skilled in the art using the methods described herein. A laboratory can establish a range of levels of oxidized high density lipoprotein (HDL) products that are characteristic for either an individual free of, or not susceptible to, a pathological condition, such as a cardiovascular disease, or who are not predisposed for progressive disease or sequelae such as heart attack, and can also establish a range of oxidized high density lipoprotein (HDL) products in a subject prone to such conditions by measuring one or more oxidized high density lipoprotein (HDL) products in these patient populations. Furthermore, these values may be used in conjunction with other standard tests used to assess a patient's risk profile for developing cardiovascular disease, such as, but not limited to, standard blood chemistry tests for measuring levels of LDL, HDL, triglycerides, cholesterol and the like. The "reference range" may then be used in the methods of the present invention for comparative purposes when testing a patient for the presence of or the susceptibility to acquiring such conditions as outlined herein. Based on this comparison, a conclusion can be drawn as to whether a pathological condition, such as a cardiovascular disease, is present in the individual being tested. Those skilled in the art may routinely establish cut-off values suitable for differentiating individuals suffering from such conditions from individuals not suffering from such conditions.

Providing a Biological Sample for Use in the Methods of the Present Invention

In particular embodiments the assays are performed using a biological sample from the individual of interest. While the assays are applicable in humans, they are not so limited. It is believed similar oxidative damage exists essentially in all mammals and thus the assays of this invention are contemplated for veterinary applications as well. Thus, suitable individuals include, but are not limited to humans, non-human primates, canines, equines, felines, porcines, ungulates, lagomorphs, and the like.

A suitable biological sample includes a sample of a biological material, which may be selected from a whole blood sample or a derivative thereof. As used herein a blood sample includes a sample of whole blood, blood cells or a blood fraction (e.g. serum or plasma). The cells may be separated out into erythrocytes, white blood cells including monocytes, PMNs, lymphocytes and may be used as whole cells or cell lysates may be prepared. The sample may be fresh blood or stored blood (e.g. in a blood bank) or blood fractions. The sample may be a blood sample expressly obtained for the assays of this invention or a blood sample obtained for another purpose, which can be subsampled for the assays of this invention. In another embodiment, the bodily sample may be saliva or CSF.

The sample may be pre-treated as necessary by dilution in an appropriate buffer solution, heparinized, concentrated if desired, or fractionated by any number of methods including but not limited to ultracentrifugation, fractionation by fast performance liquid chromatography (FPLC), or precipitation of proteins with dextran sulfate or other methods. Any of a number of standard aqueous buffer solutions, employing one of a variety of buffers, such as phosphate, Tris, or the like, at physiological pH can be used.

Assay Formats

The methods of this invention may use assays, which may be practiced, in almost a limitless variety of formats depending on the particular needs at hand. Such formats include, but are not limited to traditional "wet chemistry" (e.g. as might be performed in a research laboratory), high-throughput assay formats (e.g. as might be performed in a pathology or other clinical laboratory), and "test strip" formats, (e.g. as might be performed at home or in a doctor's office).

Traditional Wet Chemistry

The assays of this invention can be performed using traditional "wet chemistry" approaches. Basically this involves performing the assays as they would be performed in a research laboratory. Typically the assays are run in a fluid phase (e.g. in a buffer with appropriate reagents (e.g. lipids, oxidized lipids, oxidizing agent, etc.) added to the reaction mixture as necessary. The oxidized lipid concentrations are assayed using standard procedures and instruments, e.g. as described in the examples.

High-Throughput Assay Formats

Where population studies are being performed, and/or in clinical/commercial laboratories where tens, hundreds or even thousands of samples are being processed (sometimes in a single day) it is often preferably to perform the assays using high-throughput formats. High throughput assay modalities are highly instrumented assays that minimize human intervention in sample processing, running of the assay, acquiring assay data, and (often) analyzing results. In particular embodiments, high throughput systems are designed as continuous "flow-through" systems, and/or as highly parallel systems.

Flow through systems typically provide a continuous fluid path with various reagents/operations localized at different locations along the path. Thus, for example a blood sample may be applied to a sample receiving area where it is mixed with a buffer, the path may then lead to a cell sorter that removes large particulate matter (e.g. cells), the resulting fluid may then flow past various reagents (e.g. where the reagents are added at "input stations" or are simply affixed to the wall of the channel through which the fluid flows. Thus, for example, the sample may be sequentially combined with a lipid (e.g. provided as an LDL), then an oxidation agent, an agent for detecting oxidation, and a detector where a signal (e.g. a calorimetric or fluorescent signal) is read providing a measurement of oxidized lipid.

In highly parallel high throughput systems samples are typically processed in microtiter plate formats (e.g. 96 well plates, 1536 well plates, etc.) with computer-controlled robotics regulating sample processing reagent handling and data acquisition. In such assays, the various reagents may all be provided in solution. Alternatively some or all of the reagents (e.g. oxidized lipids, indicators, oxidizing agents, etc.) may be provided affixed to the walls of the microtiter plates.

High throughput screening systems that can be readily adapted to the assays of this invention are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols. Thus, for example, Zymark Corp. provides technical bulletins describing screening systems for detecting the modulation of gene transcription, ligand binding, and the like.

"Test Strip" Assay Formats

The methods of the present invention may also utilize assays which are provided in "test well" or "test strip" formats. In "test well" or "test strip" formats, the biological sample is typically placed in the well or applied to a receiving zone on the strip and then a fluorescent or calorimetric indicator appears which, in this case, provides a measure of the level of the enzymes present or absent from the sample.

Many patents have been issued which describe the various physical arrangements for blood testing. These include systems that involve lateral or horizontal movement of the blood, as well as plasma testing. For example, U.S. Pat. Nos. 4,876, 067, 4,861,712, 4,839,297, and 4,786,603 describe test carriers and methods for analytical determination of components of bodily fluids, including separating plasma from blood using glass fibers and the like. These patents, all teach systems which require some type of rotation of test pads or a portion of the test pads during use. U.S. Pat. No. 4,816,224 describes a device for separating plasma or serum from whole blood and analyzing the serum using a glass fiber layer having specific dimensions and absorption to separate out the plasma from the whole blood for subsequent reaction. Similarly, U.S. Pat. No. 4,857,453 describes a device for performing an assay using capillary action and a test strip containing sealed liquid reagents including visible indicators. U.S. Pat. No. 4,906,439 describes a diagnostic device for efficiently and accurately analyzing a sample of bodily fluid using fluid delivery in a lateral movement via flow through channels or grooves.

Methods for Measuring Oxidized High Density Lipoprotein (HDL) Products

Oxidized high density lipoprotein (HDL) products may be measured on the basis of their biological or chemical activity and/or their mass. The following describes methods for such measurements.

Buss et al noted that 3-chlorotyrosine, a specific biomarker of the neutrophil oxidant, hypochlorous acid, was present in higher quantities in tracheal aspirates of preterm infants compared to infants having normal birth weights without respiratory distress. The level of this marker correlated strongly with myeloperoxidase activity. These studies support a role for neutrophil oxidants in the pathology of chronic lung disease. Shishehbor et al. have also done studies that demonstrate that nitrotyrosine, a specific marker for protein modification by nitric oxide derived oxidants, is enriched in atherosclerotic lesions and in low density lipoprotein derived from human atheromas (Shishehbor et al (2003), *JAMA*, 289(13): 1675-80). Yet further evidence for the role of the MPO/$H_2O_2$/halide system in human atheroslerotic lesions has been demonstrated by Malle et al. (2000), *Eur. J. Biochem.* 267: 4495-4503). Specific quantitative methods for detecting 3-chlorotyrosine, 3-bromotyrosine and 3-nitrotyrosine have been elucidated by Gaut et al. (*Anal. Biochem.* (2002), 300: 252-259). Specific quantitative methods for detecting 3-chlorotyrosine, 3-bromotyrosine and 3-nitrotyrosine have been elucidated by Gaut et al. (*Anal. Biochem.* (2002), 300: 252-259). However, PCT publication number WO9604311 discloses a monoclonal antibody to nitrotyrosine, thus providing the means for development of immunological assays for measuring this marker for oxidative damage. Another antibody to nitrotyrosine can be found in the Oxis International catalog, number 24312. Furthermore, an assay to measure nitrotyrosine is provided for by Oxis International in the BIOXYTECH®Nitrotyrosine-EIA kit (Catalog Number 21055).

Kits

The diagnostic tests and methods of the present invention provide for measuring the amounts of oxidized high density lipoprotein (HDL) products as a means of assessing the risk of an individual for having or developing a condition associated with high levels of oxidative stress-induced products, such as CVD. In a particular embodiment, one or more oxidized high density lipoprotein (HDL) products are quantitated using standard reagents and kits, which are commercially available to measure each marker individually (See above). Thus, the present invention provides a quantitative and accurate means of assessing a subject's need for antioxidative therapy, or therapy with agents that are standardly used to treat CVD, by measuring all of these parameters. To the inventor's knowledge, no other art currently exists which describes combining the concurrent non-invasive techniques and measurements described herein for assessing a subject's risk for developing CVD.

While the kits described above provide the accuracy and sensitivity necessary for measurements of oxidized high density lipoprotein (HDL) products as described in the present invention, further kits may be developed that contain the antibodies, reagents, buffers, standards and instructions for assaying both enzymes using the same format, e.g. ELISA, or a calorimetric assay. The test kits would be modified appropriately depending on whether the samples to be assayed consist of whole cells, cell lysates or a combination thereof.

In some embodiments, an assay format is provided in which binding partners such as antibodies can be obtained or prepared for the oxidized high density lipoprotein (HDL) products. Biotin-avidin, biotin-streptavidin or other biotin-binding-reagent reactions can be used to enhance or modulate the test. However, any such assay can be devised using other binding partners to the analytes, including but not limited to extracellular or intracellular receptor proteins which recognize the analytes, binding fragments thereof, hybridization probes for nucleic acids, lectins for carbohydrates, etc. The particular selection of binding partners is not limiting, provided that the binding partners permit the test to operate as described herein. The preselected analytes, when present, are detectable by binding two binding partners, one immobilized on the test strip (or whatever format the assay is provided) and another part of a conjugate. This is taken into consideration in the selection of the reagents for the assay.

If a dry test strip is desired, this may be set up in any format in which contact of the sample with the reagents is permitted and the formation and mobility of the immunocomplexes and other complexes forming therein are permitted to flow and contact an immobilized reagent at the capture line. Various formats are available to achieve this purpose, which may be selected by the skilled artisan.

The label portion of the mobile, labeled antibody to the marker may be a visible label, such as gold or latex, an ultraviolet absorptive marker, fluorescent marker, radionuclide or radioisotope-containing marker, an enzymatic marker, or any other detectable label. A visibly detectable marker or one that can be easily read in a reflectometer is preferred, for use by eye, reading or confirmation with a reflectometer. Other labels may be applicable to other semi-automated or automated instrumentation.

The conjugates of the invention may be prepared by conventional methods, such as by activation of an active moiety, use of homobifunctional or heterobifunctional cross-linking reagents, carbodiimides, and others known in the art. Preparation of, for example, a gold-labeled antibody, a conjugate between an antibody and an analyte (not an immunocomplex but a covalent attachment which allows each member to independently exhibit its binding properties), biotinylation of an antibody, conjugation of streptavidin with a protein, immobilization of antibodies on membrane surfaces, etc., are all methods known to one of skill in the art.

A kit may have at least one reagent for carrying out an assay of the invention, such as a kit comprising a conjugate between a biotin-binding reagent and an antibody to an oxidized high density lipoprotein (HDL) product. Preferably, the kit comprises all of the reagents needed to carry out any one of the aforementioned assays, whether it be homogeneous, heterogeneous, comprise a single conjugate of the marker conjugated to an antibody to the analyte, or comprise two reagents which serve this function (such as a biotinylated antibody to the analyte plus a streptavidin-marker conjugate, or a biotinylated marker plus a streptavidin conjugated to an antibody to the analyte conjugate), or whether the assay employs an immobilized antibody to the analyte and a labeled antibody to a different site on the analyte. Referring to the first analyte as analyte and the second analyte as marker, and a second binding partner as a binding partner which recognizes a different epitope than the first binding partner mentioned, the kits are non-limiting examples of those embraced herein.

In the foregoing kits, the binding partners are preferably antibodies or binding portions thereof, and both the binding partner to the analyte (the oxidized high density lipoprotein (HDL) products) and the second binding partner to the analytes capable of simultaneously binding to the analyte. The immobilized binding partner may be provided in the form of a capture line on a test strip, or it may be in the form of a microplate well surface or plastic bead. The kits may be used in a homogeneous format, wherein all reagents are added to the sample simultaneously and no washing step is required for a readout, or the kits may be used in a multi-step procedure where successive additions or steps are carried out, with the immobilized reagent added last, with an optional washing step.

The antibodies specific for the two markers may be obtained commercially, or can be produced by techniques known to those skilled in the art.

Nitro Oxidized HDL Products

NO produced by endothelial cells regulates vasomotor tone and inhibits smooth muscle cell proliferation and leukocyte adhesion (Moncada et al., (1991) *Pharmacological Reviews* 43, 109-142). The larger amounts produced by macrophages help kill microbes and tumor cells. Under pathological conditions, however, reactive nitrogen species derived from NO may injure vascular tissue (Beckman et al., (1996) *Am J Physiol* 271, C1424-1437). One important pathway may be the rapid reaction of NO with superoxide, which may simultaneously create a deficit in the amount of NO needed for normal physiology and generate the potent oxidizing intermediate $ONOO^-$. Id. Overproduction of superoxide by phagocyte and nonphagocyte NADPH oxidases (such as the NOX family of enzymes) and dysregulation of NO synthase might contribute to this pathway (Babior et al., (2002) *Arch Biochem Biophys* 397, 342-344; Chen et al., (2003) *Free Radic Biol Med* 35, 117-132). Moreover, myeloperoxidase, which is enriched in human atherosclerotic lesions (Daugherty et al., (1994) *Journal of Clinical Investigation* 94, 437-444; Sugiyama et al., (2001) *Am J Pathol* 158, 879-891), uses $NO_2^-$ derived from NO to generate reactive intermediates that form 3-nitrotyrosine in proteins in vitro (Eiserich et al., (1998) *Nature* 391, 393-397; van der Vliet et al, (1997) *J Biol Chem* 272, 7617-7625). They also peroxidize the lipid moieties of LDL, converting the lipoprotein to a form that is recognized by the macrophage scavenger receptor (Podrez et al., (1999) *J Clin Invest* 103, 1547-1560). Unregulated uptake of such modified lipoprotein may play a role in cholesterol accumulation by macrophages, a critical early step in atherogenesis.

The present invention demonstrates that HDL is oxidized by reactive nitrogen species in vivo. The data demonstrate a 5-fold higher level of 3-nitrotyrosine, a specific marker for reactive nitrogen intermediates, in HDL isolated from atherosclerotic tissue than in circulating HDL. The level of 3-nitrotyrosine in lesion HDL is similar to those previously reported for lesion LDL (Leeuwenburgh et al., (1997) *Journal of Biological Chemistry* 272, 1433-1436), indicating that both lipoproteins are nitrated to a similar extent in the human artery wall.

In immunohistochemical studies of atherosclerotic lesions, myeloperoxidase is found to co-localize with epitopes recognized by antibodies to 3-nitrotyrosine, suggesting that it is an important source of reactive nitrogen species in the artery wall. However, there is no significant correlation between levels of 3-nitrotyrosine and 3-chlorotyrosine, a specific product of myeloperoxidase (Gaut et al., (2001) *Proc Natl Acad Sci USA* 98, 11961-11966), in HDL isolated from atherosclerotic lesions, suggesting that pathways independent of myeloperoxidase also nitrate HDL in the artery wall. Alternatively, macrophage scavenger receptors might bind and internalize chlorinated HDL and nitrated HDL at different rates, altering their relative concentrations in lesion HDL (Heinecke, (2002) *Free Radic Biol Med* 32, 1090-1101). It is also possible that chlorinated HDL and nitrated HDL are extracted with different efficiencies from vascular tissue. Nitrated HDL may represent a previously unsuspected biochemical link between inflammation, nitrosative stress, and atherogenesis.

The data provided herein also demonstrate that circulating HDL is nitrated on tyrosine residues. Importantly, HDL's content of 3-nitrotyrosine is twice as high in humans with established coronary artery disease as in healthy subjects.

Myeloperoxidase is likely to use $NO_2^-$ as a physiological substrate when it generates reactive nitrogen species. Myeloperoxidase-deficient mice have a markedly lower level of free 3-nitrotyrosine than wild-type mice after intraperitoneal infection with bacteria (Gaut et al., (2002) *J Clin Invest* 109, 1311-1319). In contrast, the two strains have comparable levels of the nitrated amino acid when peritoneal inflammation is induced by cecal ligation and puncture. Although both models of intraabdominal inflammation produce an intense neutrophil response and a marked increase in the level of 3-chlorotyrosine, they differ in one important respect: levels of $NO_2^-$ and $NO_3^-$ were 20-fold higher in mice infected intraperitoneally with bacteria than in mice subjected to cecal ligation and puncture (Gaut et al., (2002) *J Clin Invest* 109, 1311-1319). These results indicate that myeloperoxidase in vivo generates oxidants that can nitrate tyrosine. They also suggest that the enzyme produces these oxidants only when levels of $NO_2^-$ and $NO_3^-$ increase substantially.

Collectively, the data provided herein indicate that reactive nitrogen species oxidize HDL in the human artery wall. Nitrated HDL also circulates in blood, and individuals suffering from clinically significant atherosclerosis contain elevated levels of the oxidized lipoprotein in their plasma.

Chloro Oxidized High Density Lipoprotein (HDL) Products

The level of 3-chlorotyrosine in HDL isolated from human atherosclerotic lesions was 6-fold higher than that in circulating HDL from human subjects. Moreover, the level of 3-chlorotyrosine was 8-fold higher in HDL isolated from plasma of subjects with coronary artery disease than in HDL from plasma of healthy subjects. Hence, HOCl derived from myeloperoxidase contributes to HDL oxidation in the artery wall. Elevated levels of 3-chlorotyrosine in circulating HDL represents a novel marker for clinically significant atherosclerosis.

HDL and lipid-free apo A-I oxidized by HOCl are less able to remove cholesterol from cells by the ABCA1 pathway than native HDL and apo A-I. Because HDL contains both phospholipids and apolipoproteins, it can remove cellular cholesterol by both ABCA1-independent and -dependent mechanisms. Treating HDL with HOCl does not inhibit cholesterol efflux by ABCA1-independent processes but significantly reduces efflux from ABCA1-expressing cells. Similarly, oxidizing lipid-free apo A-I (which removes cellular lipids exclusively by the ABCA1 pathway) with HOCl markedly reduces cholesterol efflux. This inhibitory effect is near maximal when HOCl has chlorinated 50% of the tyrosine residues in apo A-I. In contrast, treating HDL or apo A-I with hydrogen peroxide, which selectively oxidizes methionines, does not affect cholesterol efflux. Previous studies have shown that methionine oxidation fails to alter apo A-1-promoted cholesterol efflux from cultured cells (Panzenbock et al., 2000. *J Biol Chem* 275:19536-19544). HOCl oxidation of an apolipoprotein-mimetic amphipathic α-helical peptide reduced its ability to remove cellular cholesterol. Thus, myeloperoxidase-mediated chlorination of tyrosine residues in HDL apolipoproteins in the artery wall may impair cholesterol removal and enhance atherogenesis.

The primary E amino group of lysine facilitates the regioselective chlorination of tyrosine residues in the YxxK motif of apo A-I and synthetic peptides by a pathway involving a chloramine intermediate. Modeling and structural studies indicate that tyrosine and lysine residues separated by two amino acids are adjacent on the same face of an α-helix, suggesting that the YxxK motif could direct protein chlorination if it resided in an α-helix. A single tyrosine residue in the 8$^{th}$ amphipathic α-helix of apolipoprotein A-I was the major site of chlorination by HOCl and that this tyrosine resides in the YxxK motif (Bergt et al, 2004. *J Biol Chem* 279:7856-7866).

The data described herein demonstrate that oxidative species generated by phagocytes chlorinate specific tyrosine residues in apo A-I. Modification of these residues impairs the protein's ability to promote cholesterol efflux from lipid-laden macrophages, contributing to the formation of atherosclerotic lesions. Because phagocytes store NADPH oxidase and myeloperoxidase in their plasma membrane and secretory compartments, respectively, oxidation is likely to be tightly restricted in space by local changes in oxidant concentrations. It is important to note that apo A-I promotes cholesterol efflux from cells by interacting with ABCA1 at the plasma membrane of macrophages. Local, pericellular production of oxidants by phagocytes is a physiological mechanism for oxidizing apo A-I and inhibiting HDL function during atherogenesis. Moreover, 3-chlorotyrosine in HDL protein may serve as a molecular fingerprint for the pathway that mediates oxidative damage in patients suffering from coronary artery disease.

DETAILED DESCRIPTION OF THE PREFERRED EMBODIMENTS

Example 1

Materials

Myeloperoxidase (donor: hydrogen peroxide, oxidoreductase, EC 1.11.1.7) was isolated by lectin affinity and size exclusion chromatographies from human neutrophils (Heinecke et al, (1993) *Journal of Biological Chemistry* 268, 4069-4077; Hope et al., (2000) *Protein Expr Purif* 18, 269-276) and stored at −20° C. Purified enzyme had an $A_{430}/A_{280}$ ratio of 0.8 and was apparently homogeneous on SDS-PAGE analysis; its concentration was determined spectrophotometrically ($\epsilon_{430}$=0.17 M$^{-1}$ cm$^{-1}$) (Morita et al., (1986) *J. Biochem.* 99, 761-770). Cambridge Isotope Laboratories (Andover, Mass.) supplied $^{13}$C-labeled amino acids. 3-Nitro [$^{13}C_6$]tyrosine was synthesized using tetranitromethane under basic conditions, and its concentration was determined by comparison with authentic material during reverse-phase HPLC (Pennathur et al., (2001) *J Clin Invest* 107, 853-860). Sodium hypochlorite (NaOCl), trifluoroacetic acid (TFA), and HPLC-grade CH$_3$CN and methanol were obtained from Fisher Scientific (Pittsburgh, Pa.). All organic solvents were HPLC grade.

Methods

Isolation of HDL. Blood anticoagulated with EDTA was collected from healthy adults and patients with clinically and angiographically documented coronary artery disease who had fasted overnight. HDL (d=1.125-1.210 g/mL) was prepared from plasma by sequential ultracentrifugation. Isolated HDL was depleted of apo E and apo B100 by heparin-agarose chromatography (Mendez et al., (1991) *J Biol Chem* 266, 10104-10111). The Human Studies Committees at University of Washington School of Medicine and Wake Forest University School of Medicine approved all protocols involving human material.

Isolation of lesion HDL. Atherosclerotic tissue was harvested at endarterectomy, snap frozen, and stored frozen at −80° C. until analysis. Lesions from a single individual (~0.5 g wet weight) were mixed with dry ice and pulverized in a stainless steel mortar and pestle. All subsequent procedures were carried out at 4° C. Powdered tissue was suspended in 2 mL of antioxidant buffer A (138 mM NaCl, 2.7 mM KCl, 100 μM diethylenetriaminepentaacetic acid (DTPA), 100 μM butylated hydroxyl toluene (BHT), protease inhibitor cocktail (Roche Diagnostics, Mannheim, Germany), 10 mM sodium phosphate, pH 7.4) in a 2 mL centrifuge tube and rocked gently overnight. Tissue was removed by centrifugation, the supernatant was collected, and the pellet was extracted a second time with antioxidant buffer for 1 h. The pooled supernatants were centrifuged at 100,000×g for 30 min, and the pellet and uppermost lipemic layer were discarded.

HDL was isolated from the tissue extract by sequential density ultracentrifugation (d=1.063-1.210 g/mL; (47)). DTPA and BHT (each 100 μM) were included in all solutions used for lipoprotein isolation. Lesion HDL was equilibrated with buffer A (0.1 mM DTPA, 100 mM sodium phosphate, pH 7.4) using a 100 kDa cut-off filter device (Millipore, Bredford, Mass.). Apo A-I in lesion HDL was detected by Western blotting using a rabbit IgG polyclonal antibody to human apo A-I (Calbiochem, La Jolla, Calif.) followed by a horseradish peroxidase-conjugated goat anti-rabbit IgG and enhanced chemiluminescence detection. Protein was determined using the Lowry assay, with albumin as the standard (BioRad; Hercules, Calif.).

HDL oxidation in vitro. Reactions were carried out in phosphate buffer (20 mM sodium phosphate, pH 7.4, 100 uM DTPA) supplemented with 1 mg/ml HDL protein, 50 nM myeloperoxidase, 250 μM H$_2$O$_2$, and 500 μM NO$_2^-$. Reactions were initiated by addition of oxidant and terminated by adding 2.5 mM methionine and 200 nM catalase. Concentrations of HOCl and H$_2$O$_2$ were determined spectrophotometrically ($\epsilon_{292}$=350 M$^{-1}$ cm$^{-1}$ $\epsilon_{240}$=39.4 M$^{-1}$ cm$^{-1}$) (48,49). 3-Nitrotyrosine formation in a 300 μL aliquot of the reaction mixture was determined in a microplate reader by monitoring absorbance at 430 nm following the addition of NaOH to adjust the pH>9.

Immunohistochemical studies. Hearts were excised at the time of cardiac transplantation in humans with cardiomyopathy (O'Brien et al., (1998) *Circulation* 98, 519-527). Coronary artery segments obtained from hearts were fixed in neutral buffered formalin and embedded in paraffin. Atherosclerotic plaques were identified by morphological criteria. Morphology was determined from 6 μm sections stained with Movat's pentachrome stains. Macrophages, myeloperoxidase, 3-nitrotyrosine, and apo A-I were identified with monoclonal antibody HAM-56 (1:10 dilution, Dako Cytomation, Carpinteria, Calif.), rabbit polyclonal antisera (1:300 dilution; Dako), immunoaffinity-purified rabbit polyclonal antibody (1:300 dilution, Upstate), and goat polyclonal:antiserum (1:750 dilution), respectively. Single-label immunohistochemistry used previously described techniques. Nova red (Vector Laboratories, Burlingame, Calif.), which yields a red reaction product, was used as the peroxidase substrate, and cell nuclei were counterstained with hematoxylin.

Protein isolation and hydrolysis. HDL protein was precipitated with ice-cold trichloroacetic acid (10% v/v), collected by centrifugation, washed with 10% trichloroacetic acid, and delipidated twice with water/methanol/water-washed diethyl:ether (1:3:7 v/v) (Pennathur et al., (2001) *J Clin Invest* 107, 853-860). Isotopically labeled internal standards were added, and samples were hydrolyzed at 110° C. for 12 h under argon with 4 N methane sulfonic acid (Sigma, Saint Louis, Mo.) supplemented with 1% benzoic acid and 1% phenol. Amino acids were isolated from the acid hydrolysate with two sequential solid-phase extraction steps, using a C18 column followed by a Chrom P column (Supelclean SPE, Supelco Inc. Bellefonte, Pa.) (Gaut et al., (2001) *Proc Natl Acad Sci USA* 98, 11961-11966; Gaut et al., (2002) *Anal Biochem* 300, 252-259). Authentic 3-nitrotyrosine and 3-chlorotyrosine were stable to acid hydrolysis, and recovery of the amino acids from the solid phase extraction columns were >80%.

Isotope dilution GC/MS Analysis. All samples were manually injected using an on column injector and a Hewlett Packard 6890 gas chromatograph equipped with a 15 m DB-5 capillary column (0.25 mm id, 0.33 micron film thickness, J & W Scientific) interfaced with a Hewlett Packard 5973 mass detector. The t-butyl dimethylsilyl derivatives of amino acids were quantified by selected ion monitoring, using isotope dilution negative-ion chemical ionization GC/MS (Gaut et al., (2001) *Proc Natl Acad Sci USA* 98, 11961-11966; Gaut et al., (2002) *Anal Biochem* 300, 252-259). The level of 3-nitrotyrosine was quantified using the ratio between the ion of m/z 518 derived from 3-nitrotyrosine ([M-O-t-butyl-dimethylsilyl]$^-$) and the ion of m/z 524 derived from 3-nitro[$^{13}C_6$] tyrosine. The level of 3-chlorotyrosine was quantified using the ratio between the ion of m/z 489 derived from 3-chlorotyrosine ([M-Cl-t-butyl-dimethylsilyl]$^-$) and the ion of m/z 495 derived from 3-chloro[$^{13}C_6$]chlorotyrosine. Potential artifact formation was monitored as the appearance of ions at m/z 528 (nitration) or m/z 499 (chlorination) derived from L-[$^{13}C_9$, $^{15}N$]tyrosine added prior to sample work-up. Under these experimental conditions, artifact formation was <20% of 3-nitrotyrosine and <5% of 3-chlorotyrosine. L-Tyrosine is present at 10.000-fold higher levels than the oxidation products. Therefore the sample was diluted 1:100 and analyzed in a separate injection. L-Tyrosine and L-[$^{13}C_6$]tyrosine were quantified using the ions ([M-CO$_2$—t-butyl-dimethylsilyl]$^-$) at m/z 407 and m/z 413, respectively. Under these chromatography conditions, authentic products and isotopically labeled standards were baseline-separated and exhibited retention times identical to those of analytes derived from tissue samples. The limit of detection (signal/noise >10) was <1 femtomol for all the amino acids.

Statistical analysis. Results represent means±SEM. Differences between two groups were compared using an unpaired Student's t-test. Correlations were determined using linear regression analysis for nonparametric data (Sigma Stat, SPSS). A P value <0.05 was considered significant.

Results

Myeloperoxidase generates 3-nitrotyrosine in HDL protein under physiologically relevant in vitro conditions. To determine whether myeloperoxidase can nitrate tyrosine residues on HDL protein, we incubated the lipoprotein with the enzyme at neutral pH in phosphate buffer containing $NO_2^-$ (500 µM) and $H_2O_2$ (250 µM). We monitored the formation of 3-nitrotyrosine spectroscopically by quantifying absorbance of the alkalinized reaction mixture at 430 nm.

3-Nitrotyrosine was readily detected in HDL exposed to the complete myeloperoxidase-$H_2O_2$—$NO_2^-$ system. Nitration required each component of the reaction mixture: $NO_2^-$, $H_2O_2$, and myeloperoxidase (FIG. 1A). The reaction depended on $NO_2$-concentration over a range of 0-1000 µM (FIG. 1B) and was complete in 20 min (FIG. 1C). It was inhibited by the peroxide scavenger catalase (200 nM) (FIG. 1C) and the heme poison sodium azide (10 mM) (data not shown). These results indicate that myeloperoxidase nitrates HDL by a reaction that requires active enzyme, $NO_2^-$, and $H_2O_2$.

Myeloperoxidase generates 3-nitrotyrosine by directly oxidizing $NO_2$. It has been proposed that myeloperoxidase uses at least two distinct pathways to generate reactive nitrogen species (Eiserich et al., (1996) *Journal of Biological Chemistry* 271, 19199-19208). In the first pathway, the enzyme uses $H_2O_2$ and Cl$^-$ to generate HOCl, which then reacts with $NO_2^-$ to form nitryl chloride, a nitrating species. In the second pathway, myeloperoxidase uses a one-electron reaction to directly oxidize $NO_2^-$ to nitrogen dioxide radical, $NO_2^*$. The radical might then oxidize tyrosine directly or might react with the tyrosyl radical that myeloperoxidase also generates (38,53).

Figure 2:
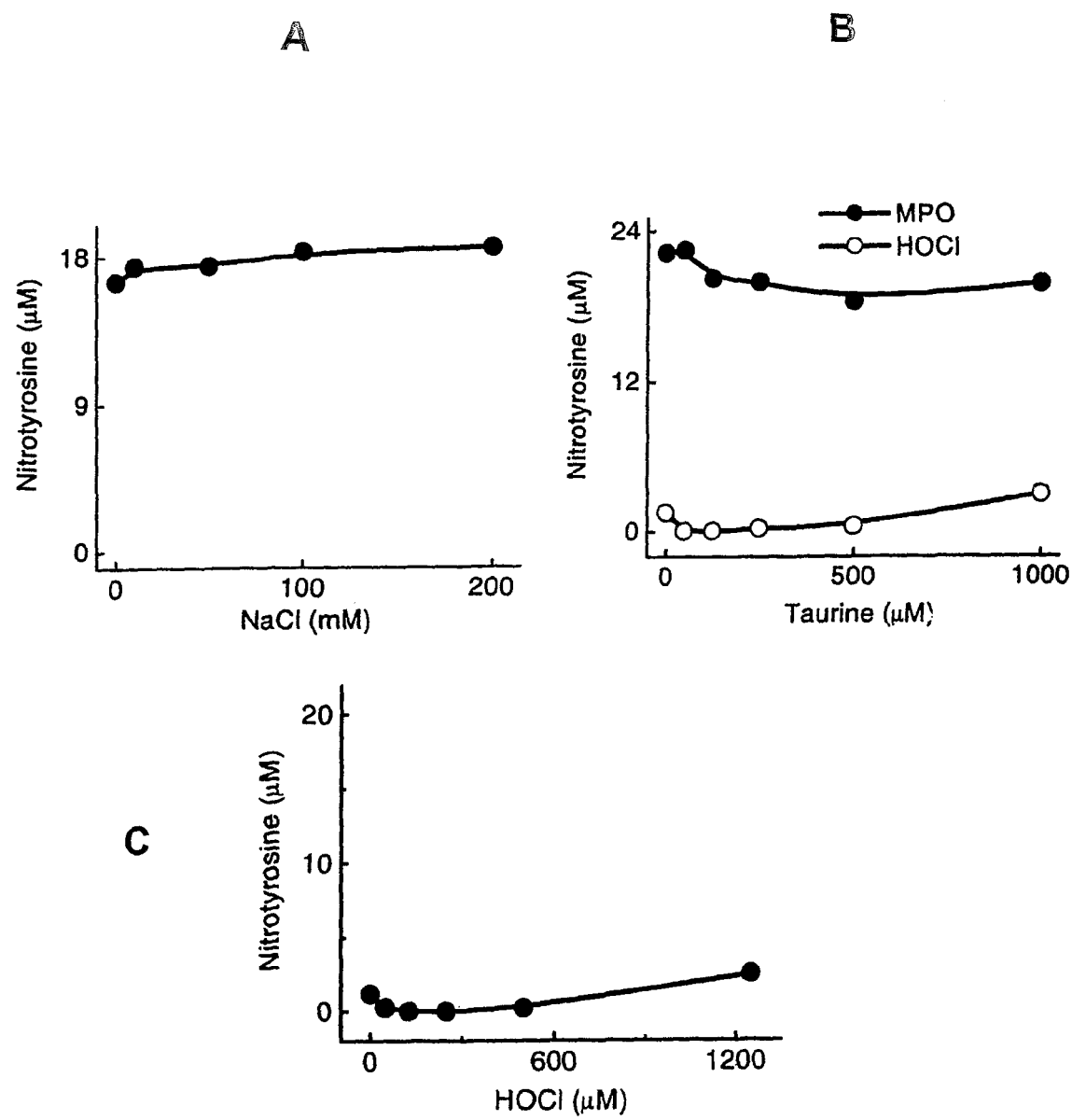
FIG. 2 describes the effect of $Cl^-$ or taurine on HDL nitration by the myeloperoxidase-$H_2O_2$—$NO_2^-$ system or HOCl—$NO_2^-$. HDL was exposed for 60 min at 37° C. to myeloperoxidase in phosphate buffer supplemented with 250 μM $H_2O_2$, 500 μM $NO_2^-$ and (A) the indicated concentration of $Cl^-$ or (B) the indicated concentration of taurine and 100 mM $Cl^-$. (C) HDL was exposed for 60 min at 37° C. in phosphate buffer containing 500 μM $NO_2^-$ and the indicated concentration of HOCl.

To distinguish between these two pathways, we examined the effect of plasma concentrations of chloride ion (Cl$^-$) on nitration of HDL by the myeloperoxidase-$H_2O_2$—$NO_2^-$ system (FIG. 2). We also determined whether taurine (2-aminoethanesulfonic acid), a potent scavenger of HOCl, inhibited nitration by the myeloperoxidase or HOCl—$NO_2^-$. The extent of HDL nitration by myeloperoxidase was independent of Cl$^-$ (FIG. 2A). Taurine also had no effect when myeloperoxidase nitrated HDL in the presence of Cl$^-$ (FIG. 2B). Moreover, we were unable to detect 3-nitrotyrosine in HDL exposed to HOCl—$NO_2^-$ (FIG. 2C). These observations indicate that HOCl produced by myeloperoxidase is not a major contributor to the nitration of HDL.

Instead, the pathway likely involves direct oxidation of $NO_2^-$ by compound I (a complex of myeloperoxidase and $H_2O_2$) and the reaction of the resulting $NO_2^*$ with tyrosyl radical (van Dalen et al., (2000) *J Biol Chem* 275, 11638-11644). It is noteworthy that myeloperoxidase preferentially oxidizes $NO_2^-$ under these conditions, despite the presence of 200-fold greater levels of Cl$^-$.

Myeloperoxidase co-localizes with 3-nitrotyrosine in human atherosclerotic lesions. To determine whether apo A-I might be nitrated in vivo, we used immunohistochemical methods to study coronary arteries harvested from patients undergoing cardiac transplantation (n=8). Apo A-I was rarely detected in nonatherosclerotic segments of these coronary arteries (data not shown). In contrast, the vast majority of lesions contained extracellular deposits of apo A-I (FIG. 3A), indicating that this protein is a characteristic component of atherosclerotic tissue (O'Brien et al., (1998) *Circulation* 98, 519-527).

Myeloperoxidase immunoreactivity was very prominent in intimal mononuclear cells. We detected such positive cells in all regions of atheroma, though immunoreactivity was especially evident in the subendothelial space, fibrous cap, and lipid core as well as near microvessels. We also detected extracellular myeloperoxidase immunoreactivity, both around macrophages (FIG. 3D) and in the lipid core of advanced atheromatous plaques (data not shown).

Figure 3:
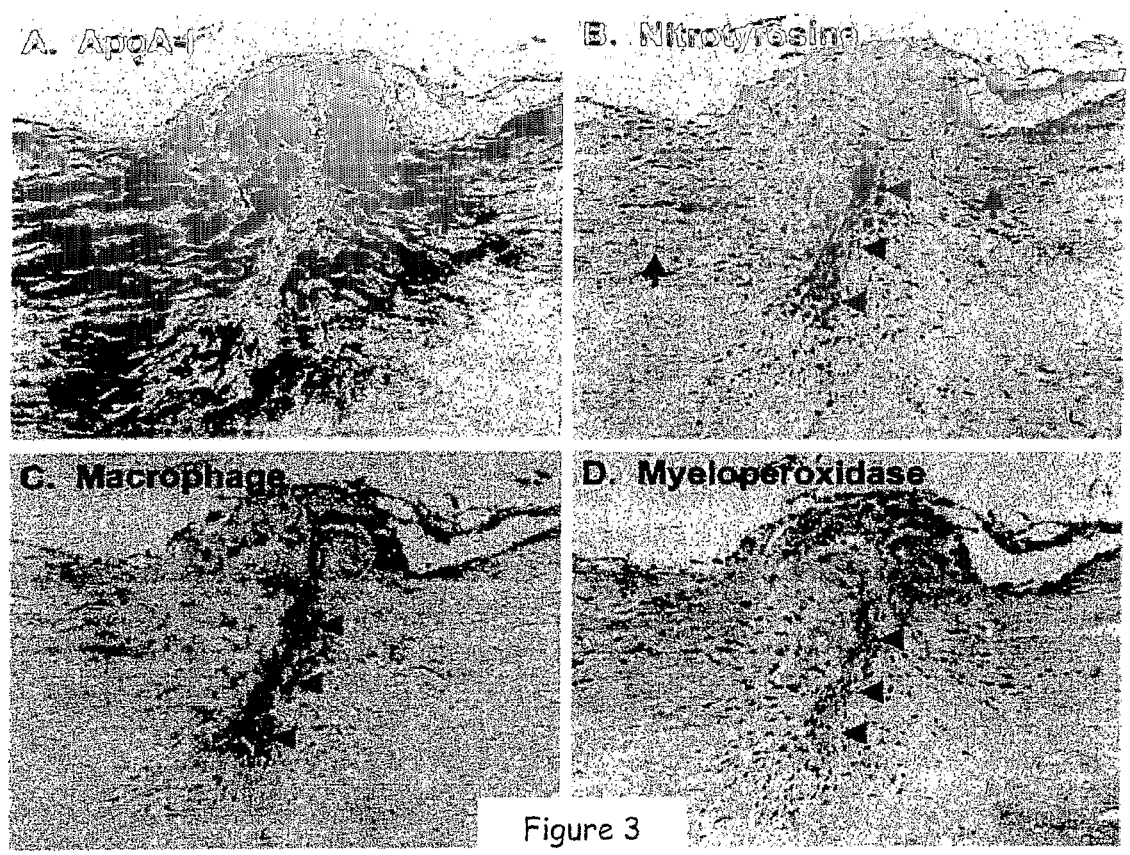
FIG. 3 describes immunohistochemical co-localization of apo A-I and proteins modified by reactive nitrogen species in human atherosclerotic plaque. Photomicrographs of neighboring sections of human coronary arteries harvested at cardiac transplant. Atherosclerotic plaque was immunostained for apoA-I (A), proteins containing 3-nitrotyrosine (B), macrophages (C), and myeloperoxidase (D). Positive immunohistochemical staining is indicated by a red immunoreaction product. Original magnification, 100×; hematoxylin counterstain.

To establish which cells express myeloperoxidase, we immunostained atherosclerotic tissue with antibodies to myeloperoxidase and HAM-56, a specific marker for macrophages. Most myeloperoxidase-positive cells reacted with HAM-56, indicating that they were macrophages (FIG. 3C). Advanced plaques contained many cells that were positive for both myeloperoxidase and HAM-56, though some HAM-56-positive macrophages were negative for myeloperoxidase.

These results indicate that human atherosclerotic lesions contain a major population of macrophages that express myeloperoxidase.

To determine whether reactive intermediates from myeloperoxidase might nitrate intimal proteins, we compared patterns of immunostaining for 3-nitrotyrosine and myeloperoxidase. These patterns were virtually identical (FIGS. 3B,D). Antibodies to both 3-nitrotyrosine and the enzyme reacted with material that associated closely with macrophages or was in the macrophages themselves. These observations raise the possibility that apo A-I is targeted for nitration in atherosclerotic intima. They also support the proposal that myeloperoxidase is an important pathway for generating 3-nitrotyrosine in the human artery wall.

Figure 4:
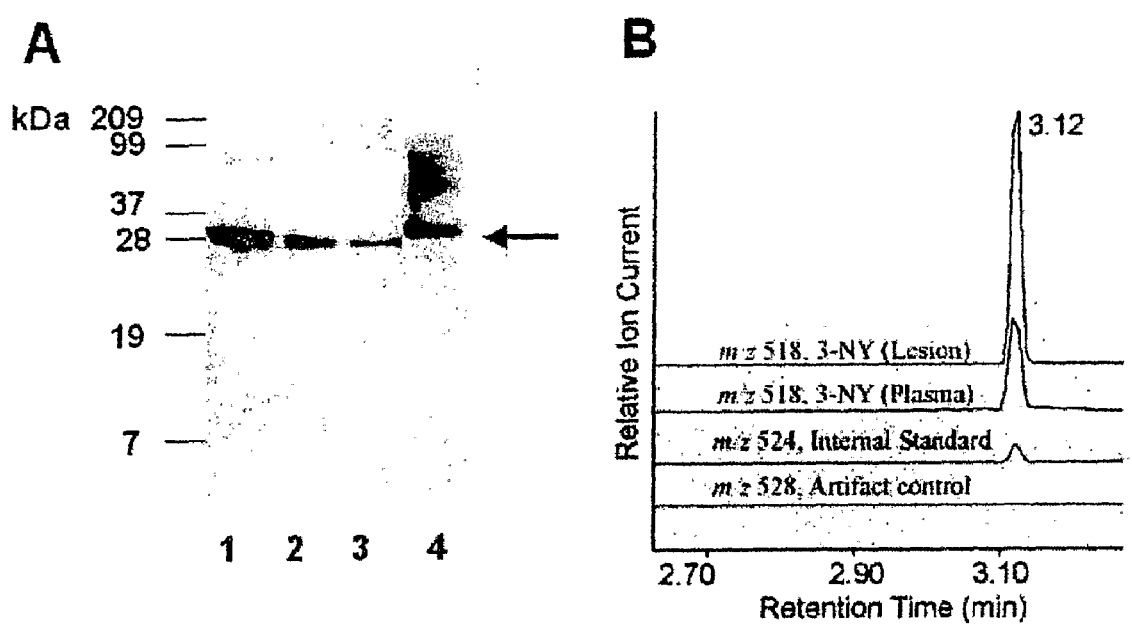
FIG. 4 demonstrates the detection by mass spectrometry of 3-nitrotyrosine in HDL isolated from plasma and atherosclerotic human aortic tissue harvested at surgery. Human atherosclerotic tissue was obtained at surgery from subjects undergoing carotid endarterectomy. Atherosclerotic lesions were frozen in dry ice and pulverized. Powdered tissue was suspended overnight in buffer (containing antioxidants and metal chelators) at 4° C. HDL was isolated from the suspension by sequential ultracentrifugation. $^{13}$C-Labeled internal standards were added, and the protein was hydrolyzed with acid. (A) Western blot analysis of HDL isolated from lesions and plasma with an antibody specific for apo A-I. Plasma HDL (lanes 1-3), 0.5, 0.1 and 0.05 μg protein. Lesion HDL (lane 4), 1 μg protein. Arrow, monomeric apo A-I. (B) Amino acids derived from HDL were isolated on a C18 solid-phase column, derivatized, and analyzed by isotope dilution negative-ion electron capture GC/MS with selected ion monitoring.

HDL isolated from human atherosclerotic lesions contains 3-nitrotrosine. To determine whether reactive nitrogen species damage lipoproteins in vivo, we quantified 3-nitrotyrosine in lesion HDL. We isolated the HDL by sequential ultracentrifugation from atherosclerotic tissue that was freshly harvested from patients undergoing carotid endarterectomy. To prevent artifactual oxidation of lipoproteins, we used buffers containing high concentrations of DTPA (a metal chelator) and BHT (a lipid soluble antioxidant). Western blotting with a monospecific rabbit antibody confirmed that lesion HDL contained a high concentration of apo A-I and a range of apparently larger immunoreactive proteins (FIG. 4A). Quantitative Western blotting demonstrated that apo A-I accounted for >50% of the protein in the HDL.

To quantify 3-nitrotyrosine, isolated HDL was delipidated, hydrolyzed, and the amino acids in the hydrolysate isolated by solid-phase extraction on a C18 column. The reisolated amino acids were derivatized and analyzed by GC/MS with selected ion monitoring in the negative-ion chemical ionization mode. The derivatized amino acids isolated from lesion HDL contained a compound that exhibited the major ion identical to that of authentic 3-nitrotyrosine. Selected ion monitoring showed that this ion (FIG. 4B) co-eluted with the ion derived from $^{13}$C-labeled internal standard (3-nitro[$^{13}C_6$] tyrosine). In contrast, there was little evidence for 3-nitrotyrosine formation during sample work-up and analysis (3-nitro [$^{13}C_9$,$^{15}$N]tyrosine; FIG. 4B). These results indicate that 3-nitrotyrosine is present in HDL isolated from human atherosclerotic lesions and that it is not an artifact of sample preparation.

Figure 5:
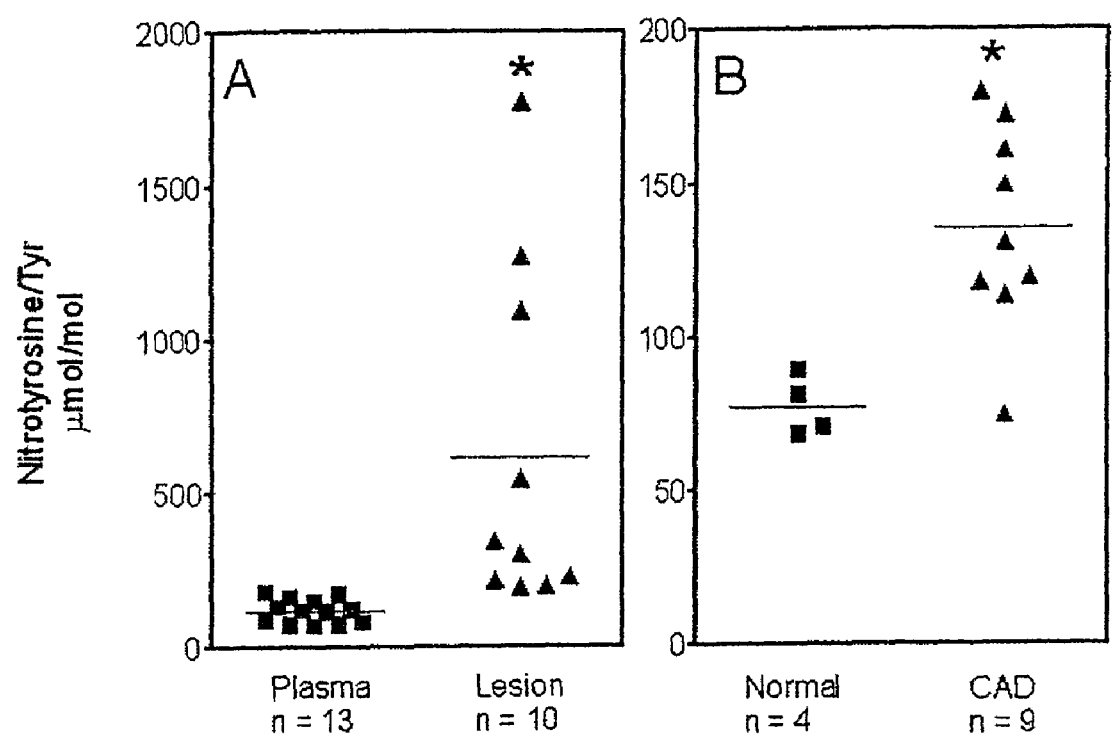
FIG. 5 demonstrates the mass spectrometric quantification of 3-nitrotyrosine in HDL isolated from plasma and human atherosclerotic lesions. Plasma was obtained from healthy humans and humans with established coronary artery disease. Human atherosclerotic tissue was obtained at surgery from subjects undergoing carotid endarterectomy. HDL was isolated from plasma and atherosclerotic aorta by sequential ultracentrifugation. $^{13}$C-Labeled internal standards were added, and the protein was hydrolyzed with acid. Derivatives of the oxidized amino acids were quantified by isotope dilution negative-ion electron capture GC/MS with selected ion monitoring.

HDL isolated from human atherosclerotic lesions is enriched in 3-nitrotrosine. To assess quantitatively the contribution of nitration to the oxidation of artery wall lipoproteins, we isolated HDL from plasma of healthy humans and from human atherosclerotic aortic tissue. HDL was delipidated and hydrolyzed, the resulting amino acids were isolated and derivatized, and the derivatized amino acids were quantified with isotope dilution GC/MS with selected ion monitoring (FIG. 5A). The concentration of 3-nitrotyrosine in HDL isolated from the atherosclerotic lesions was 5 times higher (619±178 μmol/mol Tyr; n=10) than that in circulating HDL (118±39 lμmol/mol Tyr; n=13; P<0.01). These observations provide strong evidence that HDL is one target for damage by reactive nitrogen intermediates in the human artery wall.

HDL modified by reactive nitrogen species circulates in the blood of humans with established coronary artery disease. To determine whether nitrated HDL also circulates in blood, we used isotope dilution GC/MS to quantify 3-nitrotyrosine levels in HDL isolated by sequential ultracentrifugation from the blood of healthy humans and humans with established atherosclerosis. The subjects with atherosclerosis had lesions documented by clinical symptoms and coronary angiography. The healthy subjects were normolipidemic with no known history of coronary artery disease.

Circulating HDL isolated from patients with established atherosclerosis contained a 2-fold higher concentration of 3-nitrotyrosine (136±1 μmol/mol Tyr; n=9) than circulating HDL (78±5 μmol/mol Tyr; n=4) isolated from the healthy humans (FIG. 5B; P<0.01). These observations provide strong evidence that human blood contains nitrated HDL and that 3-nitrotyrosine levels in circulating HDL are higher in humans with clinically established coronary artery disease than in healthy humans.

Figure 6:
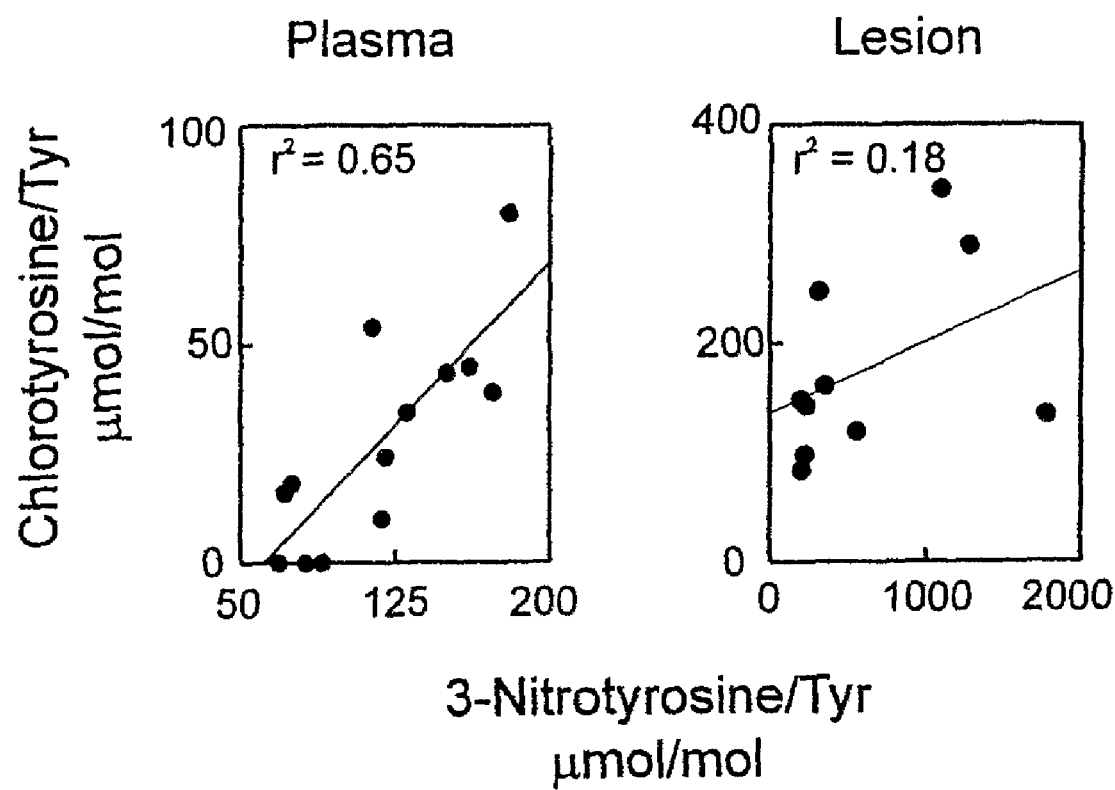
FIG. 6 demonstrates the association between 3-nitrotyrosine and 3-chlorotyrosine levels in HDL isolated from human atherosclerotic lesions or plasma. Levels of oxidized amino acids in HDL were determined in lesion HDL and circulating HDL as described in the legend to FIG. 5.

Levels of 3-nitrotyrosine correlate strongly with those of 3-chlorotyrosine in circulating HDL but not lesion HDL. To determine whether myeloperoxidase might promote protein nitration in vivo, we assessed the relationship between 3-chlorotyrosine, a marker of protein oxidation that is generated only by myeloperoxidase at plasma concentrations of halide ion, and levels of 3-nitrotyrosine in both circulating and lesion HDL (FIG. 6).

Linear regression analysis demonstrated a strong correlation between levels of 3-chlorotyrosine and levels of 3-nitrotyrosine ($r^2$=0.65; P<0.01) in plasma HDL. In contrast, there was no significant correlation ($r^2$=0.18; P=0.15) between levels of 3-chlorotyrosine and those of 3-nitrotyrosine in lesion HDL. These observations strongly support the hypothesis that myeloperoxidase promotes the formation of 3-chlorotyrosine and 3-nitrotyrosine in circulating HDL but suggest that other pathways also produce 3-nitrotyrosine in atherosclerotic tissue.

Example 2

Materials. Cambridge Isotope Laboratories (Andover, Mass.) supplied $^{13}$C-labeled amino acids. 3-Chloro[$^{13}C_6$]tyrosine was synthesized using HOCl under acidic conditions, and its concentration was determined by comparing it with authentic material in reverse-phase HPLC (Gaut et al., 2002. Anal Biochem 300:252-259.). All organic solvents were HPLC grade. Carotid endarterectomy tissue was supplied by the Division of Vascular Surgery, Bowman Grey School of Medicine. Vascular tissue resected at surgery was immediately frozen at −80° C. until analysis.

Protein Oxidation Reactions. Reactions were carried out at 37° C. in PBS (10 mM sodium phosphate, 138 mM NaCl, 2.7 mM KCl, pH 7.4) supplemented with 1 mg/mL HDL protein. Reactions were initiated by adding oxidant and terminated by adding a 10- to 50-fold molar excess of L-methionine. Concentrations of HOCl and $H_2O_2$ were determined spectrophotometrically ($\epsilon_{292}$=350 $M^{-1}$ $cm^{-1}$ and $\epsilon_{240}$=39.4 $M^{-1}$ $cm^{-1}$) (Morris, 1966. J Phys Chem 70:3798-3805; Nelson, 1972. Anal Biochem 49:474-478. Protein was determined using the Lowry assay (BioRad; Hercules, Calif.) with albumin as the standard.

Isolation of HDL. Blood collected from healthy adults and patients with documented coronary artery disease who had fasted overnight was anticoagulated with EDTA to obtain plasma. HDL (d=1.125-1.210 g/mL) was prepared by sequential ultracentrifugation and was depleted of apo E and apo B 100 by heparin-agarose chromatography (Mendez et al., 1991. J Biol Chem 266:10104-10111).

Lesion HDL was isolated from carotid endarterectomy specimens that had been snap frozen. Lesions from a single individual (0.5 g wet weight) were frozen in dry ice and pulverized with a stainless steel mortar and pestle. All subsequent procedures were carried out at 4° C. Tissue powder was suspended in 2 mL of buffer A (0.15 M NaCl, 100 μM diethylenetriaminepentaacetic acid (DTPA), 100 μM butylated hydroxyl toluene (BHT), protease inhibitor cocktail (Roche Diagnostics, Mannheim, Germany), 10 mM sodium phosphate, pH 7.4) in a 2 mL centrifuge tube and rocked gently overnight. Tissue was removed by centrifugation, the supernatant was collected, and the pellet was extracted a second time with buffer A for 1 h. The pooled supernatants were centrifuged at 100,000×g for 30 min, and the pellet and uppermost lipemic layer were discarded. HDL was isolated from the tissue extract by sequential density ultracentrifugation (d=1.063-1.210 g/mL; (Mendez et al., 1991. *J Biol Chem* 266:10104-10111). DTPA and BHT (both 100 µM) were included in all solutions used for lipoprotein isolation. Lesion HDL was equilibrated with buffer B (0.1 mM DTPA, 50 mM sodium phosphate, pH 7.4) using a 100 kDa cut-off filter device (Millipore, Bredford, Mass.). Apo A-I in lesion HDL was immunodetected using polyclonal rabbit anti-(human apo A-I) IgG followed by a horseradish peroxidase conjugated goat anti-rabbit IgG and enhanced chemiluminescence detection.

Immunohistochemical Studies. Human coronary artery segments were obtained from hearts excised at the time of cardiac transplantation, then fixed in neutral buffered formalin and embedded in paraffin. Atherosclerotic plaques were identified by morphological criteria in 6 µm sections stained with Movat's pentachrome stains. Macrophages, myeloperoxidase, HOCl-modified proteins, and apo A-I were respectively identified with monoclonal antibody HAM-56 (1:10 dilution, Dako Cytomation, Carpinteria, Calif.), rabbit polyclonal antisera (1:300 dilution; Dako), hybridoma cell culture supernatant (HOP-1), and goat polyclonal antiserum (1:750 dilution). HOP-1 (clone 2D10G9) was provided by Dr. Malle (Medical University Graz, Graz, Austria). Single-label immunohistochemistry was performed using previously described techniques (O'Brien et al., 1998. *Circulation* 98:519-527). Nova red (Vector Laboratories, Burlingame, Calif.), which yields a red reaction product, was used as the peroxidase substrate, and cell nuclei were counterstained with hematoxylin.

Mass Spectrometric Analysis. HDL protein was precipitated with ice-cold trichloroacetic acid (10% v/v), collected by centrifugation, washed with 10% trichloroacetic acid, and delipidated twice with water/methanol/water-washed diethyl:ether (1:3:7 v/v) (33). Isotopically labeled internal standards were added, and samples were hydrolyzed at 110° C. for 12 h under argon with 4 N methane sulfonic acid (Sigma, Saint Louis, Mo.) supplemented with 1% benzoic acid and 1% phenol. Amino acids were isolated from the acid hydrolysate with two sequential solid-phase extraction steps using a C-18 column followed by a Chrom P column (Supelclean SPE, Supelco Inc. Bellefonte, Pa.) (Gaut et al. 2001. *Proc Natl Acad Sci USA* 98:11961-11966; Gaut et al., 2002. *Anal Biochem* 300:252-259.). The t-butyl dimethylsilyl derivatives of amino acids were quantified by selected ion monitoring using isotope dilution negative-ion chemical ionization GC/MS performed on a Hewlett Packard 6890 gas chromatograph equipped with a 15 m DB-5 capillary column (0.25 mm id, 0.33 micron film thickness, J & W Scientific) and interfaced with a Hewlett Packard 5973 mass detector. Under these chromatography conditions, authentic compounds and isotopically labeled standards were baseline-separated and exhibited retention times identical to those of analytes derived from tissue samples. The limit of detection (signal/noise >10) was <1 femtomol for all the amino acids. Authentic 3-chlorotyrosine was stable to acid hydrolysis and recovery of the amino acid from the solid phase extraction columns was >80%.

All samples were manually injected using an on column injector. The level of chlorotyrosine was quantified using the ratio between the ion of m/z 489 derived from 3-chlorotyrosine ([M-Cl-t-butyl-dimethylsilyl]$^-$) and the ion of m/z 495 derived from 3-chloro[$^{13}C_6$]chlorotyrosine. Potential artifact formation was monitored as the appearance of ions at m/z 499 derived from L-[$^{13}C_9$,$^{15}N$]tyrosine added prior to sample work up. Under our experimental conditions, artifact formation was <5% of total 3-chlorotyrosine. To quantify L-tyrosine, which is present at 10.000-fold higher levels than the oxidation products, the sample was diluted 1:100 and analyzed in a separate injection. L-Tyrosine and L-[$^{13}C_6$]tyrosine were quantified using the ions ([M-COO-t-butyl-dimethylsilyl]$^-$) at m/z 407 and m/z 413, respectively.

Two-Dimensional Liquid Chromatography—Tandem MS Analysis. LC-ESI-MS/MS analyses were performed in the positive ion mode with a Finnigan Mat LCQ ProteomeX ion trap instrument (San Jose, Calif.) coupled to a Surveyor (Finnigan, San Jose, Calif.) quaternary HPLC pump, which in turn was interfaced with a strong cation exchange resin and a reverse-phase column (McDonald, W. H., and Yates, J. R., 3rd. 2002. *Dis Markers* 18:99-105.). A fully automated 8-cycle chromatographic run was carried out on each sample. The SEQUEST algorithm was used to interpret MS/MS spectra. Matches were visually assessed if unique peptides had highly significant SEQUEST scores (Id.).

Cell Culture and Cholesterol Efflux. Baby hamster kidney (BHK) cells expressing mifepristone-inducible human ABCA1 were generated as previously described (35). Cellular cholesterol was labeled by adding 1 µCi/mL [$^{31}H$]cholesterol (NEN Life Science Products) to the growth medium. Twenty four hours later, strong expression of ABCA1 was induced by incubating the cells for 20 h with DMEM containing 1 mg/mL bovine serum albumin (DMEM/BSA) and 1 nM mifepristone (Vaughan et al., 2003. *J Lipid Res* 44:1373-1380). To measure cholesterol efflux, mock- or ABCA1-transfected cells were incubated with DMEM/BSA without or with HDL, apo A-I, or peptide. After 2 to 4 h, the medium and cells were assayed for [$^3H$]cholesterol as described (Id.). Cholesterol efflux mediated by HDL, apo A-I, or peptide was calculated as the percentage of total [$^{31}H$]cholesterol (medium plus cell) released into the medium after subtracting the value obtained with DMEM/BSA alone.

Statistical analysis. Results represent means±SD. Differences between two groups were compared using an unpaired Student's t-test. Multiple comparisons were performed using one-way analysis of variance (ANOVA; Graph Pad software, San Diego, Calif.). A P value <0.05 was considered significant.

Results

Figure 7:
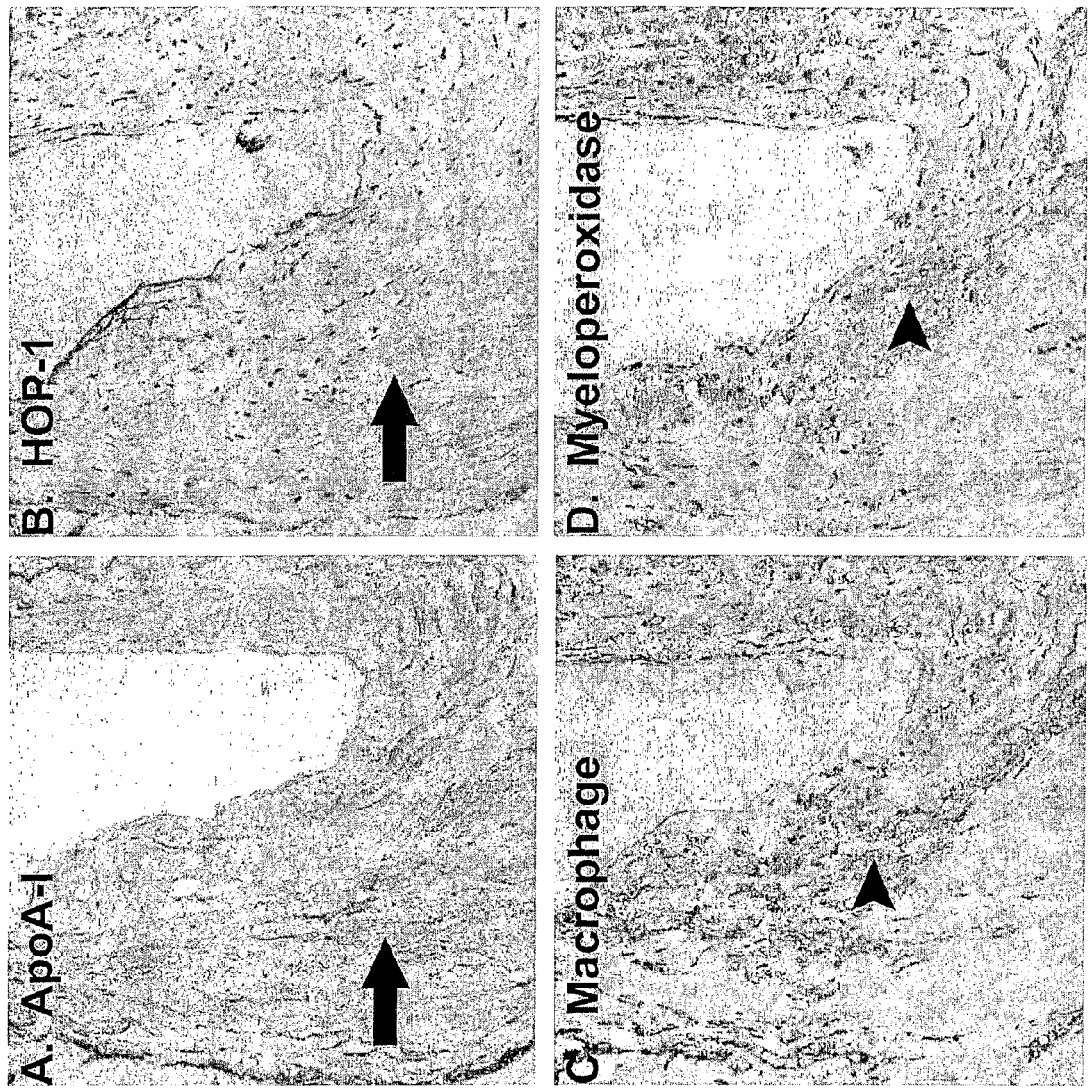
FIG. 7 describes Immunohistochemical analysis of apo A-I, myeloperoxidase, and proteins modified by HOCl in human atherosclerotic intima. Photomicrographs of adjacent sections of an atherosclerotic coronary artery demonstrating immunostaining for apo A-I (A), proteins modified by HOCl (B), macrophages (C), and myeloperoxidase (D). Positive immunohistochemical staining is indicated by a red reaction product. HOCl-modified epitopes co-localize with extracellular apo A-I (arrows, A and B), while myeloperoxidase staining is primarily associated with macrophages (arrowheads, C and D). Original magnification, 100×; hematoxylin counterstain.

Apo A-I Co-localizes with HOCl Adducts in Human Atherosclerotic Tissue. To determine whether HOCl might modify HDL in vivo, we used antibodies specific for apo A-I and HOCl-modified proteins to immunostain coronary arteries obtained from patients undergoing cardiac transplantation (O'Brien et al., 1998. *Circulation* 98:519-527). Apo A-I co-localized with epitopes recognized by HOP-1, an antibody specific for proteins oxidized by HOCl (Hazell et al., 1996. *J Clin Invest* 97:1535-1544.), in the intima of atherosclerotic lesions (FIGS. 7 A,B).

It was demonstrated previously that myeloperoxidase is present in atherosclerotic lesions, in both macrophage-associated and extracellular distributions (Daugherty et al., 1994. *J Clin Invest* 94:437-444.). The vast majority of cell-associated myeloperoxidase immunoreactivity was present in macrophages, and most of the extracellular myeloperoxidase was juxtaposed with macrophages (FIGS. 7C,D). HOCl-modified proteins also co-localized with macrophages. However, the most robust staining for HOCl-modified proteins was extracellular and co-localized with apo A-I. These observations are consistent with HOCl's ability to generate long-lived reactive intermediates such as chloramines, which can diffuse long distances to react with proteins. Indeed, chloramines mediate tyrosine chlorination in apo A-I in vitro (Bergt et al., 2004. *J Biol Chem* 279:7856-7866.). The co-localization of HOCl-modified proteins with apo A-I suggests that HOCl oxidizes specific proteins in the human artery wall.

Figure 8:
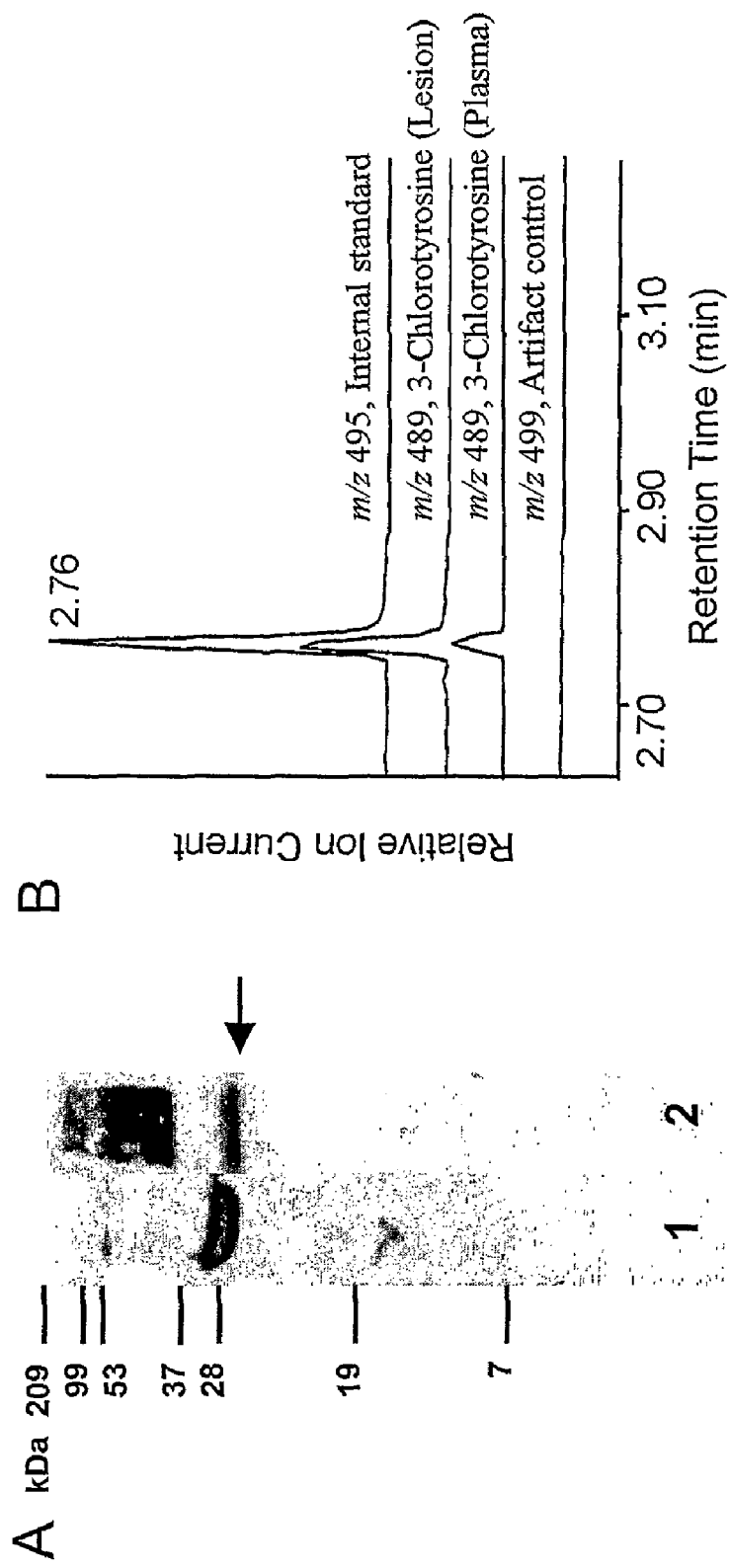
FIG. 8 describes mass spectrometric detection of 3-chlorotyrosine in HDL isolated from atherosclerotic human tissue harvested at surgery. Atherosclerotic tissue was obtained from subjects undergoing carotid endarterectomy. HDL was isolated from the supernatant of tissue powder by sequential ultracentrifugation. $^{13}$C-Labeled internal standards were added, and the protein was hydrolyzed with acid. (A) Western blot analysis of circulating HDL (1) and lesion HDL (2) with an antibody monospecific for apo A-I. Arrow, monomeric apo A-I. (B) Analysis of derivatized amino acids derived from HDL by isotope dilution negative-ion electron capture GC/MS with selected ion monitoring.

3-Chlorotyrosine is Elevated in HDL Isolated from Human Vascular Lesions. To quantitatively assess whether myeloperoxidase oxidizes proteins in the artery wall, we isolated HDL by sequential density gradient ultracentrifugation from human carotid atherosclerotic tissue recovered at surgery. Lesion HDL subjected to immunoblotting analysis with a rabbit polyclonal antibody monospecific for human apo A-I demonstrated a protein with the predicted molecular mass of apo A-I (FIG. 8A). Forms of immunoreactive apo A-I with higher molecular mass were also present. Monomeric apo A-I represented >50% of lesion HDL protein as assessed by Western blotting.

We used negative-ion chemical ionization GC/MS to determine whether 3-chlorotyrosine was present in HDL isolated from human atherosclerotic lesions. To confirm that any 3-chlorotyrosine detected in HDL was endogenous rather than artifactual, an isotope-labeled tyrosine (L-[$^{13}C_9,^{15}N$] tyrosine) was routinely added to each sample before analysis. We reasoned that any procedure that converted endogenous tyrosine to 3-chlorotyrosine would also convert L-[$^{13}C_9,^{15}N$] tyrosine to 3-chloro[$^{13}C_9,^{15}N$]tyrosine. The latter would be detectable by GC/MS because its mass-to-charge ratio (m/z) differs from those of 3-chlorotyrosine and the internal standard.

A compound was detected in the amino acid hydrolysate that exhibited major ions and retention times identical to those of authentic 3-chlorotyrosine. Selected ion monitoring showed that the ions derived from this amino acid co-eluted with those derived from 3-chloro[$^{13}C_6$]tyrosine (FIG. 2B). In contrast, there was little evidence for 3-chlorotyrosine formation during sample work-up and analysis (3-chloro [$^{13}C_9,^{15}N$]tyrosine).

These results indicate that HDL isolated from human atherosclerotic lesions contains 3-chlorotyrosine, a specific marker of chlorination by myeloperoxidase.

Figure 9:
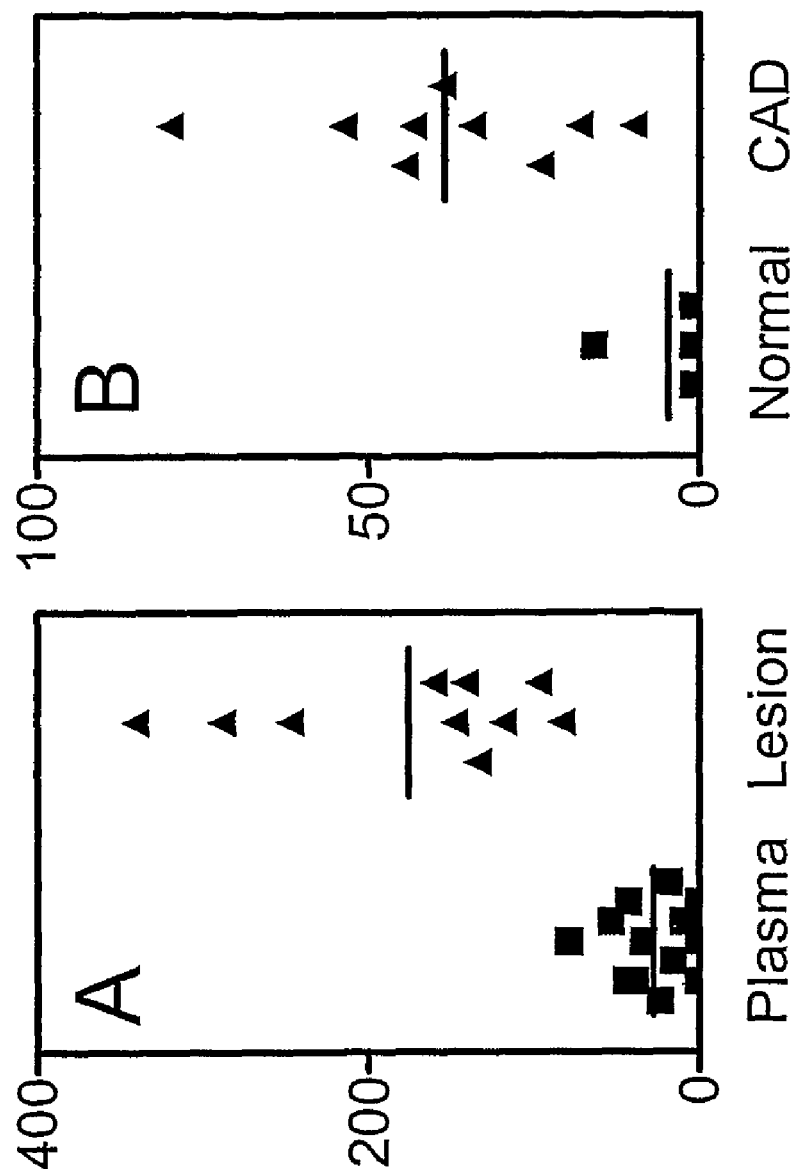
FIG. 9 describes Mass spectrometric quantification of 3-chlorotyrosine in HDL isolated from plasma and human atherosclerotic lesions. Plasma was obtained from healthy humans and humans with established coronary artery disease (CAD). Human atherosclerotic tissue was obtained at surgery from subjects undergoing carotid endarterectomy. HDL was isolated from plasma and atherosclerotic carotid tissue by sequential ultracentrifugation. Oxidized amino acids isolated from hydrolyzed HDL proteins were quantified by isotope dilution negative-ion electron capture GC/MS with selected ion monitoring.

HDL was isolated from human plasma and from human atherosclerotic aortic tissue. After delipidating and hydrolyzing the proteins, levels of the derivatized amino acid in acid hydrolysates were quantified with isotope dilution GC/MS (FIG. 9A). Remarkably, there was six fold higher level of protein-bound 3-chlorotyrosine in lesion HDL (177±27 µmol/mol Tyr; n=10) than in circulating HDL (28±7 µmol/mol Tyr; n=13) isolated from humans (P<0.001).

Figure 10:
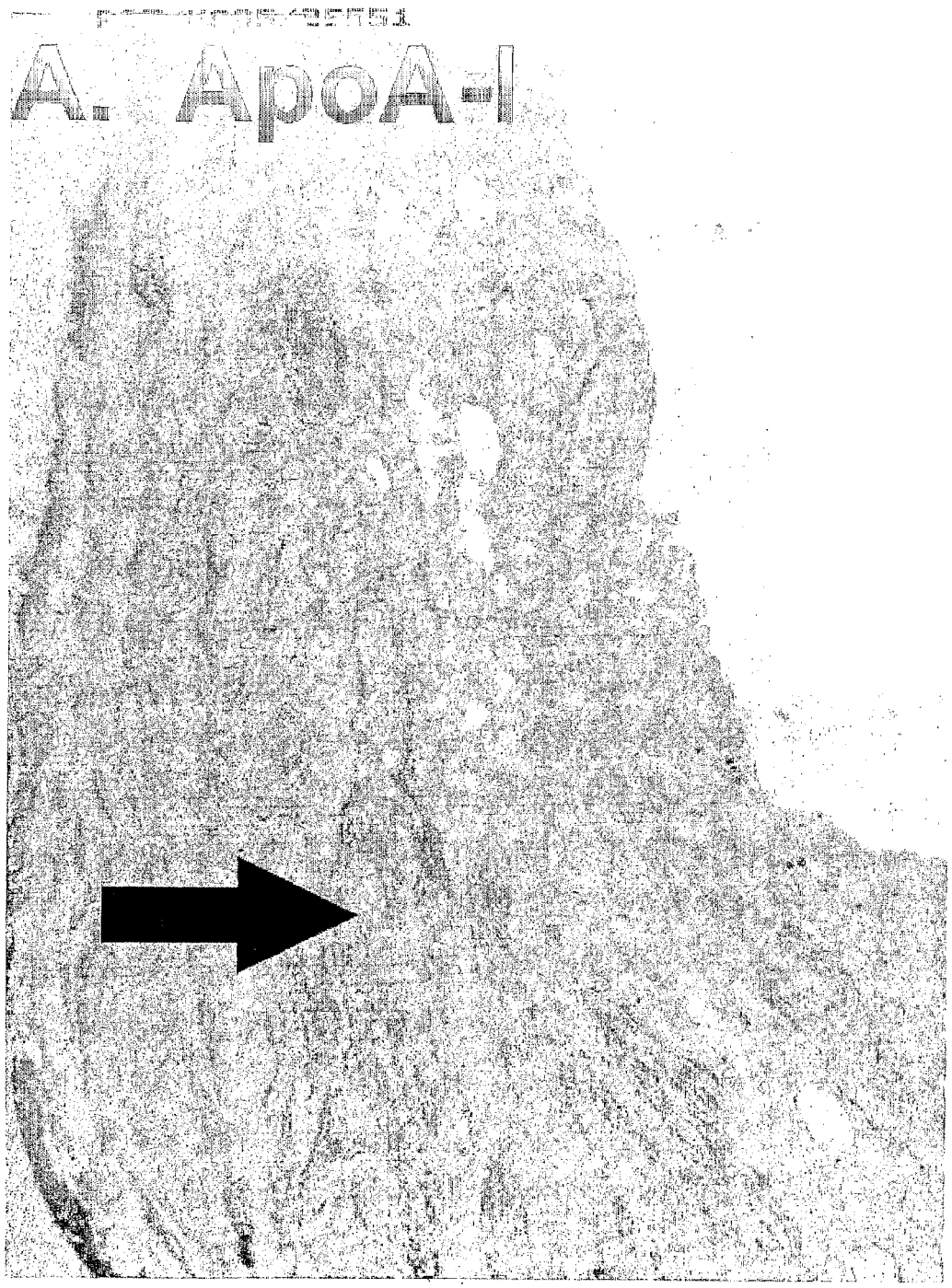
FIG. 10 describes detection of myeloperoxidase in lesion HDL by 2-dimensional liquid chromatography tandem mass spectrometric analysis. HDL isolated from human lesions was digested with trypsin and subjected to LC-ESI-MS/MS analysis. Four peptides unique to myeloperoxidase were identified. The MS/MS spectrum of one peptide (WDGERLYQEARK) is shown.

HDL Isolated from Human Atherosclerotic Lesions Contains Myeloperoxidase. Previous studies have shown that LDL binds myeloperoxidase under physiologically relevant conditions (Carr et al., *FEBS Lett* 487:176-180). To determine whether HDL in the artery wall might behave similarly, we digested lesion HDL with trypsin and analyzed the resulting peptides with 2-D liquid chromatography and ESI-MS. Four peptides in the digest were derived from myeloperoxidase. Their origin was confirmed by sequencing them with MS/MS (FIG. 10). This observation provides strong evidence that myeloperoxidase is a component of HDL isolated by ultracentrifugation from atherosclerotic lesions and suggests that the enzyme has high affinity for HDL in the artery wall.

Levels of 3-Chlorotyrosine Are Elevated in Plasma HDL from Humans with Coronary Artery Disease. To determine whether oxidized HDL might also be present in the circulation, we isolated HDL from plasma of healthy subjects (4 males, ages 34-63) and subjects with established coronary artery disease (7 males and 2 females, ages 33-67). The former had no known history of vascular disease or symptoms suggestive of angina, peripheral vascular disease, or cerebral vascular disease. The subjects with coronary artery disease had angiographically documented atherosclerosis.

To determine whether levels of chlorinated lipoproteins were elevated in the subjects with coronary artery disease, we isolated HDL from their plasma and plasma of healthy subjects. After delipidating and hydrolyzing the proteins, we subjected the derivatized amino acid hydrolysate to isotope dilution GC/MS analysis (FIG. 9B). The level of protein-bound 3-chlorotyrosine was 8-times higher in circulating HDL from the patients (39±7 µmol/mol Tyr; n=9) than in circulating HDL from the healthy subjects (5±4 lµmol/mol Tyr; n=4; P=0.01). Levels of chlorinated HDL (perhaps derived from vascular lesions) are elevated in the blood of humans suffering from clinically significant atherosclerosis.

Oxidation of HDL and Apo A-I Impairs Cholesterol Transport in Cultured Cells by ABCA1. The 10 amphipathic helices in apolipoprotein A-I, HDL's major protein, are thought to play essential roles in lipid binding, lipoprotein stability, and reverse cholesterol transport (Segrest et al., 1992. *J Lipid Res* 33:141-166; Brouillette et al., 2001. *Biochim Biophys Acta* 1531:4-46.). Five of the 7 tyrosine residues in this protein lie in amphipathic helices, and we have previously shown that Tyr192 in helix 8 is the major site of chlorination (Bergt et al., 2004. *J Biol Chem* 279:7856-7866.). We therefore hypothesized that HOCl might alter the ability of HDL and apo A-I to remove cholesterol from cells.

We exposed HDL or purified apo A-I to HOCl or $H_2O_2$ (80:1 or 25:1, mol/mol, oxidant:HDL particle or oxidant:apo A-I) in a physiological buffer (138 mM NaCl, 2.7 mM KCl, 10 mM sodium phosphate) at neutral pH for 120 min at 37° C., terminating the reaction with a 20-fold molar excess (relative to oxidant) of methionine. Because the average $HDL_3$ particle contains 2 mol of apolipoprotein A-I (7 tyrosine residues, 243 amino acids) and 1 mol of apolipoprotein A-II (8 tyrosine residues, 154 amino acids), the ratio of oxidant to substrate (mol:mol) was 30:1 for apolipoproteins A-I and A-II, 3:1 for tyrosine residues, and 1:8 for total amino acids. For lipid-free apo A-I, the ratio of oxidant to substrates was 30% greater than for apo A-I in HDL. We previously showed that 50% of Tyr192 is chlorinated by HOCl under these conditions (Bergt et al., 2004. *J Biol Chem* 279:7856-7866).

Figure 11:
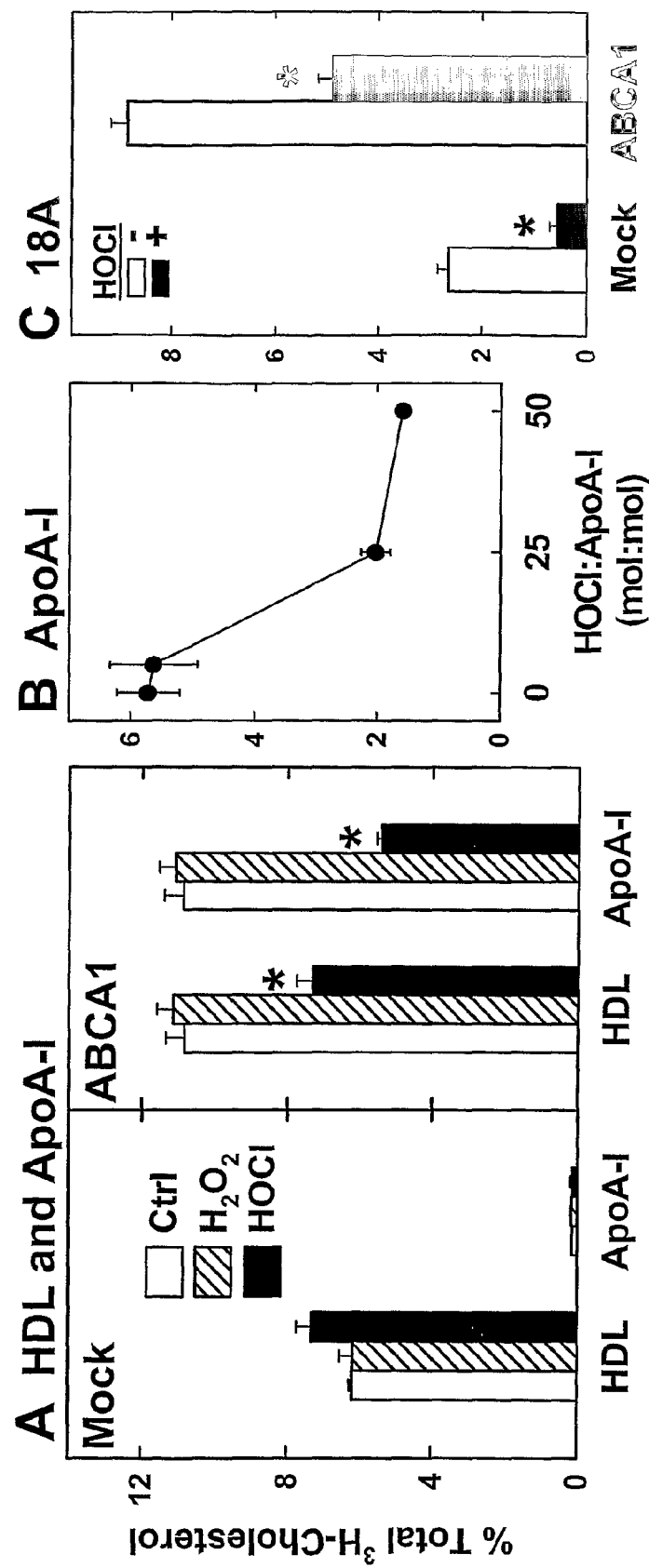
FIG. 11 describes cholesterol efflux activities of native and HOCl-oxidized HDL, apo A-I, and peptide 18A. [$^3$H]Cholesterol-labeled mock-(A, C) or ABCA1-transfected (A-C) BHK cells were incubated for 4 h with native (Ctrl), $H_2O_2$-oxidized, or HOCl-oxidized HDL (20 □g/mL) or apo A-I (5 □g/mL) (A), for 2 h with 5 □g/mL apo A-I oxidized with the indicated mole ratio of HOCl (B), or for 2 h with control (−) or HOCl-oxidized (+) peptide Ac-18A-$NH_2$ (20 □g/mL) (C). At the end of the incubation, [$^3$H]cholesterol efflux to the acceptor particle was measured. *$P<0.01$ compared with controls.

We next determined how oxidation affects the ability of HDL or apo A-I to promote cholesterol efflux from BHK cells that expressed very low or very high levels of ABCA1. With mock-transfected cells (low ABCA1), HDL promoted cholesterol efflux exclusively by diffusional mechanisms, and apo A-I had essentially no cholesterol efflux activity (FIG. 5A). Oxidation of HDL with HOCl or $H_2O_2$ (which oxidizes methionines) had no effect on or slightly increased HDL-mediated cholesterol efflux from these cells. When ABCA1 was overexpressed in transfected BHK cells, however, HDL-mediated cholesterol efflux increased and apo A-I became active (FIG. 11A). Whereas $H_2O_2$ oxidation had no effect, chlorination was associated with a significant decrease in the cholesterol efflux that was promoted by HDL or apo A-I (FIGS. 11A, B). These observations indicate that oxidation of HDL and apo A-I with HOCl selectively impairs their abilities to remove cholesterol from cells by a pathway requiring ABCA1.

Oxidation of a Synthetic Peptide Containing Tyrosine Impairs Lipid Efflux Ability. Acetyl-18A-NH$_2$ (18A), an 18-amino-acid analog of the type of amphipathic α-helix found in apolipoproteins, mimics apo A-I in promoting cholesterol efflux by the ABCA1 pathway (Mendez et al., 1994. *J Clin Invest* 94:1698-1705; Remaley et al. 2003. *J Lipid Res* 44:828-836). 18A contains a single tyrosine residue in a KxxY motif (where K=lysine, Y=tyrosine, and x=an amino acid unreactive with HOCl), which juxtaposes the amino acid side chains of K and Y residues in an α-helical peptide. Mass spectrometric analysis revealed that ~50% of the tyrosine residues in 18A were chlorinated when it was exposed to HOCl (5:1, oxidant/peptide, mol/mol).

We investigated the ability of native and oxidized 18A to promote cholesterol efflux from BHK cells. In contrast to apo A-I, 18A promoted cholesterol efflux from both mock- and ABCA1-transfected BHK cells, but to a much greater extent from the ABCA1-expressing cells. HOCl treatment significantly reduced 18A's ability to remove cholesterol by both the ABCA1-independent and -dependent mechanisms (FIG. 11C). Site-specific oxidation of tyrosines in amphipathic α-helices can impair lipid transport activities.

Example 3

Approximately 40% of renal transplants are performed in diabetics. These patients are at high risk for atherosclerosis and approximately 50% of the transplants are lost due to cardiovascular mortality in these patients despite acceptable renal graft function. Kidney disease has been linked to risk of recurrent cardiovascular disease and mortality. See, Shlipak et al, *NEJM*, (2004) 352(20):2049; Coresh et al., (2005) *Circulation and Hemodynamics* 10:73; Weiner et al., *American Journal of Kidney Diseases* (2004) 44(2):198; Anavekar et al., (2004) *NEJM* 351(13):1285; Go et al., *NEJM* (2004) 351(13):1296. We postulated that oxidative stress is increased in the diabetic renal transplant patient population.

Methods

We divided a study population into 2 groups according to non-diabetic control patients who have undergone a renal transplant and diabetic patients who have undergone a renal transplant. Ten patients were included in each group. Serum creatinine levels were measured for patients in each group to verify that there was no significant difference between the two groups (mean 1.7 vs 1.62 mg/dL). The mean HbA1C for the diabetic patients was 8.3. End stage renal disease (ESRD) secondary to diabetes was a prerequisite to be enrolled in the diabetic arm. All patients were required to have stable renal function for at least 3 months after renal transplant, creatinine <1.8 mg/dl (estimated creatinine clearance by CG formula of >50 ml/min), proteinuria <250 mg/day based on average of three measurements of spot protein/creatinine ratio, no active infection or evidence of rejection and no clinically active coronary artery disease (CAD).

We measured the levels of oxidized amino acids in serum and urine at 3 months, 6 months and 9 months post transplantation in the diabetics thereby accumulating 3 data points per patient and 6 months and 9 months in the non-diabetics thereby accumulating 2 data points per patient.

Two-Dimensional Liquid Chromatography—Tandem MS Analysis. LC-ESI-MS/MS analyses were performed in the positive ion mode with a Finnigan Mat LCQ ProteomeX ion trap instrument (San Jose, Calif.) coupled to a Surveyor (Finnigan, San Jose, Calif.) quaternary HPLC pump, which in turn was interfaced with a strong cation exchange resin and a reverse-phase column (McDonald, W. H., and Yates, J. R., 3rd. 2002. *Dis Markers* 18:99-105). A fully automated 8-cycle chromatographic run was carried out on each sample. The SEQUEST algorithm was used to interpret MS/MS spectra. Matches were visually assessed if unique peptides had highly significant SEQUEST scores (Id.).

Statistical analysis. Results represent means±SD. Differences between the two patient populations were compared using an unpaired Student's t-test. Multiple comparisons were performed using one-way analysis of variance (ANOVA; Graph Pad software, San Diego, Calif.). A P value <0.05 was considered significant.

HDL was isolated from urine, human plasma and from human atherosclerotic aortic tissue in patients having undergone renal transplant and in control patients. After delipidating and hydrolyzing the proteins, levels of the derivatized amino acid in acid hydrolysates were quantified with isotope dilution GC/MS pursuant to the protocols outlined in Example 2.

Figure 12:
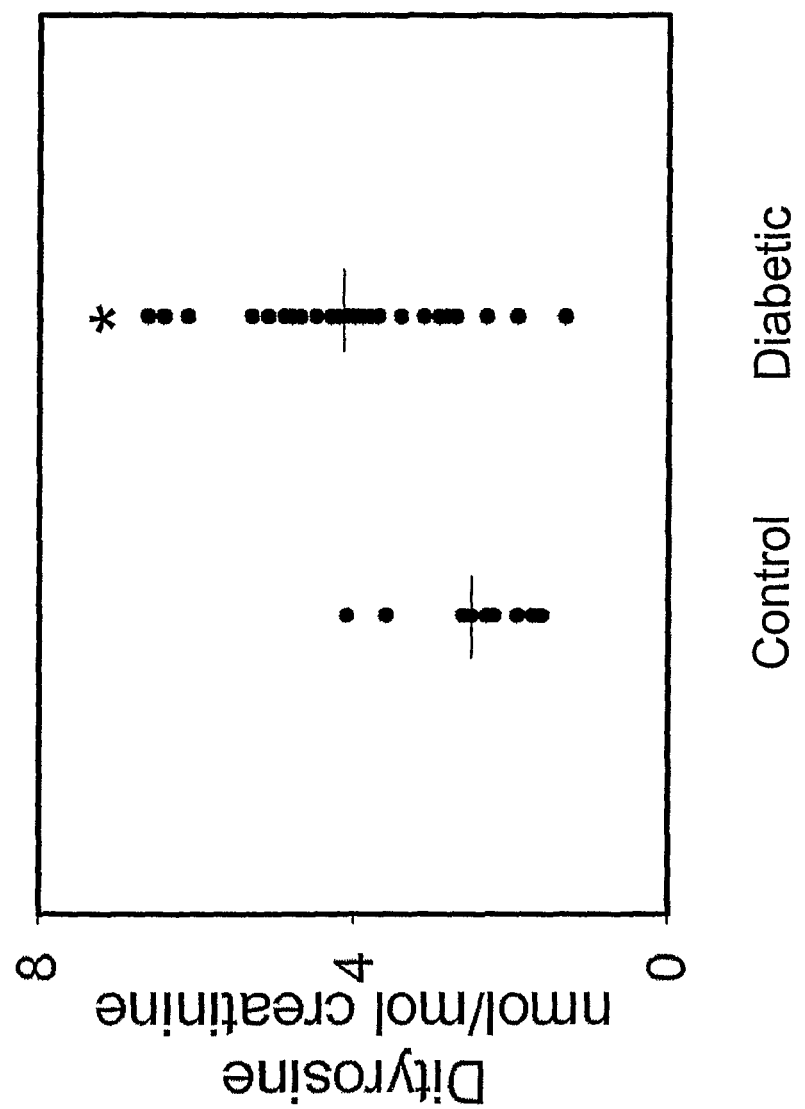
FIG. 12 depicts dityrosine levels present in the urine in control patients and diabetic patients having undergone a renal transplant. The urinary dityrosine levels in nmol/mol creatinine are elevated about 50% in the diabetic patients having undergone a renal transplant.
Figure 13:
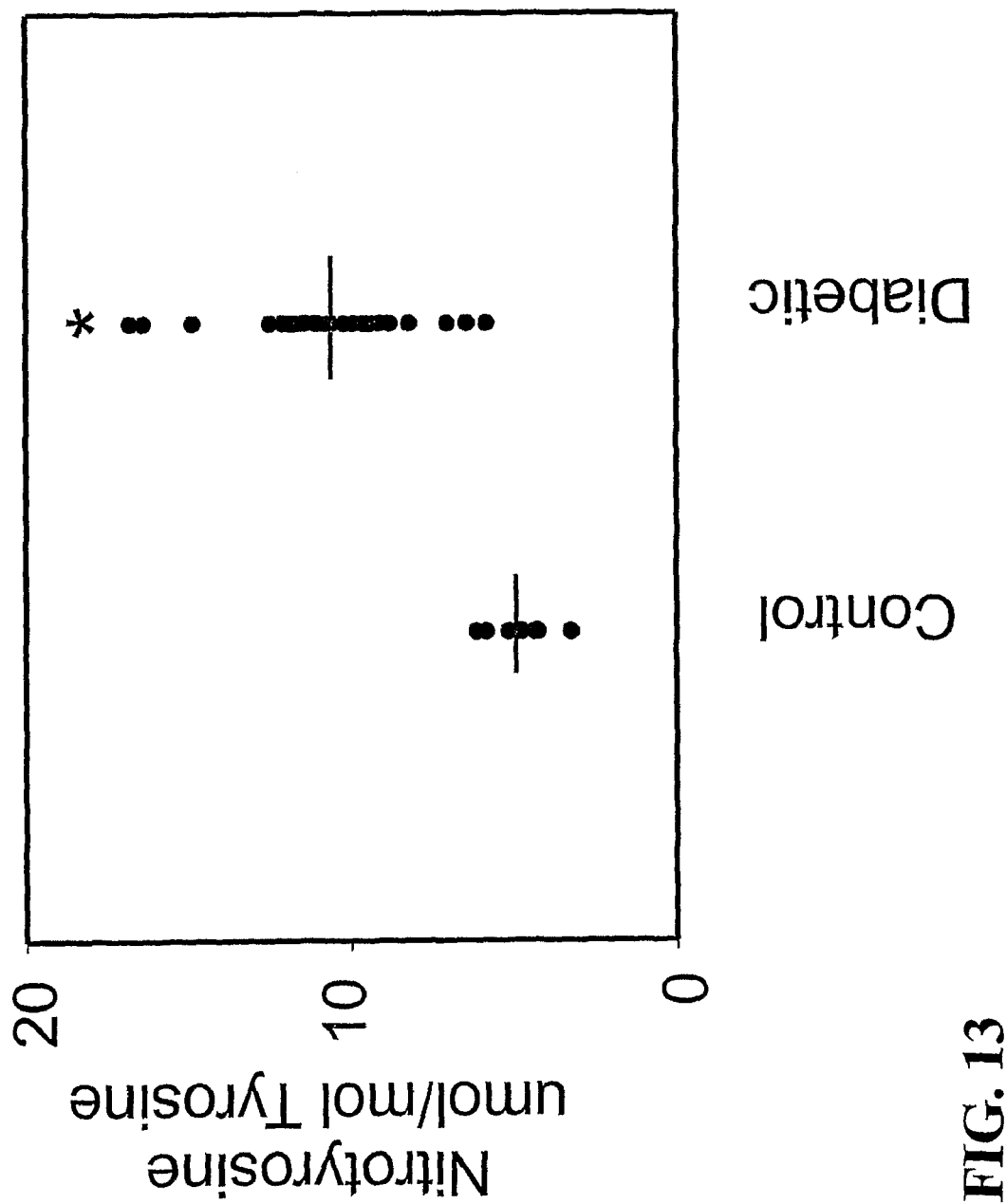
FIG. 13 depicts nitrotyrosine levels present in the plasma in control patients and diabetic patients having undergone a renal transplant. The plasma nitrotyrosine levels in umol/mol tyrosine are elevated about 100% in the diabetic patients having undergone a renal transplant as compared to control patients. HDL was isolated from the plasma by sequential ultracentrifugation. $^{13}$C-labeled internal standards were added, and the protein was hydrolyzed with acid. Derivatives of the oxidized amino acids were quantified by isotope dilution negative-ion electron capture GC/MS with selected monitoring. Results are normalized to the protein content of L-tyrosine, the precursor of 3-nitrotyrosine and 3-chlorotyrosine.
Figure 14:
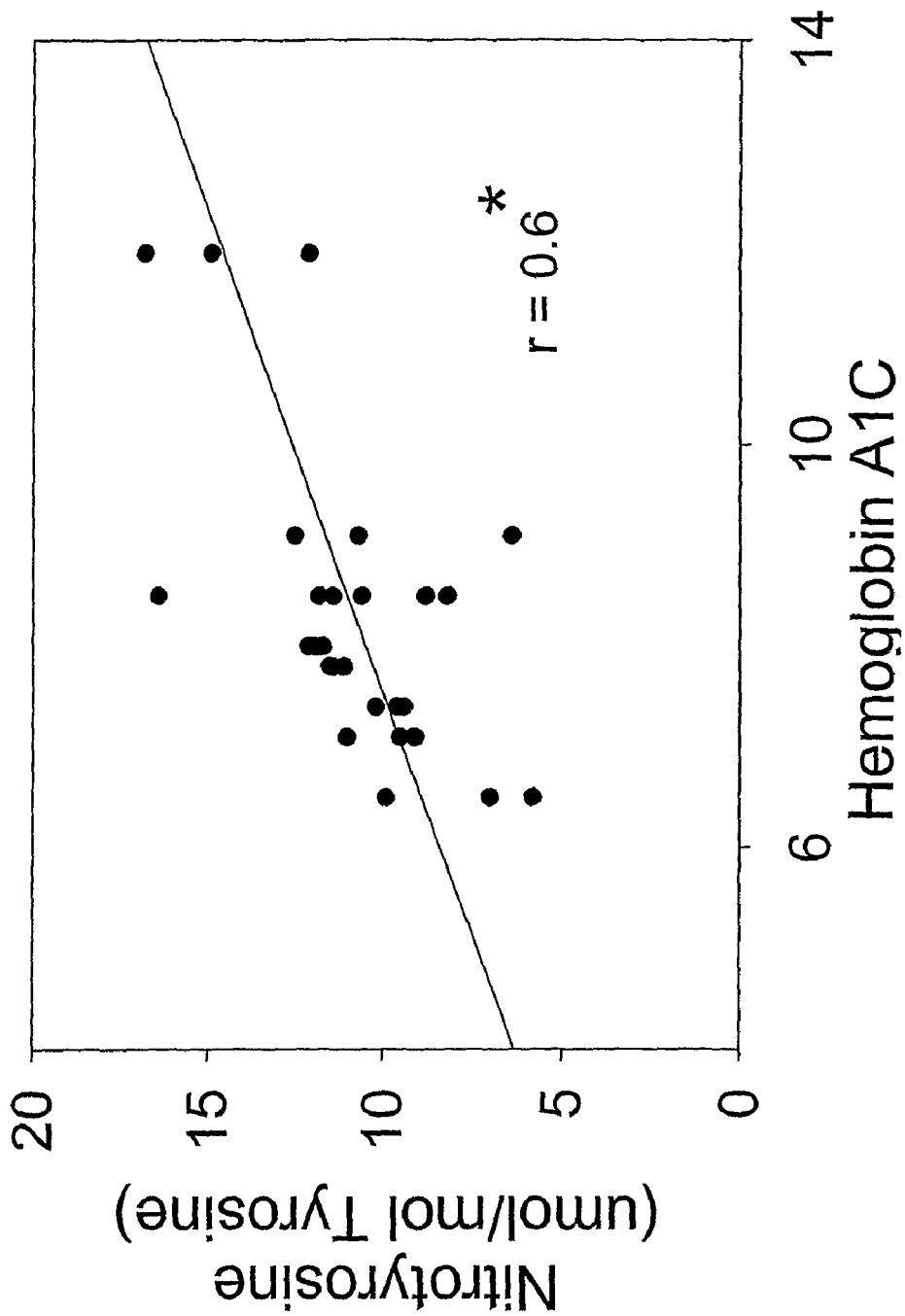
FIG. 14 depicts the correlation between nitrotyrosine levels present in the plasma in control patients and diabetic patients having undergone a renal transplant and levels of Hemoglobin A1C. The plasma nitrotyrosine levels are presented in umol/mol tyrosine.
Figure 15:
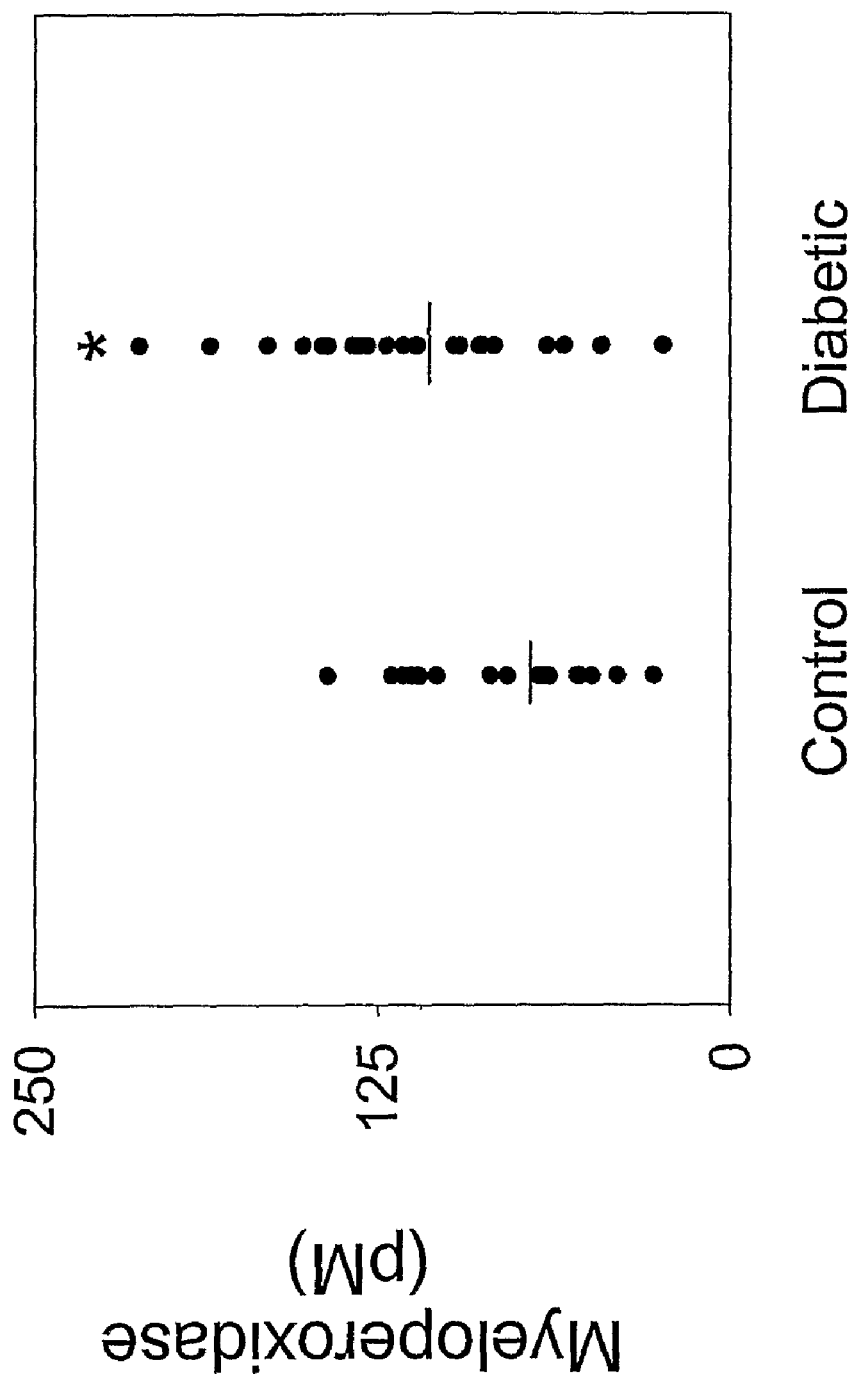
FIG. 15 depicts myeloperoxidase levels present in the plasma in control patients and diabetic patients having undergone a renal transplant. The plasma myeloperoxidase levels in pM are elevated in the diabetic patients having undergone a renal transplant as compared to control patients.
Figure 16:
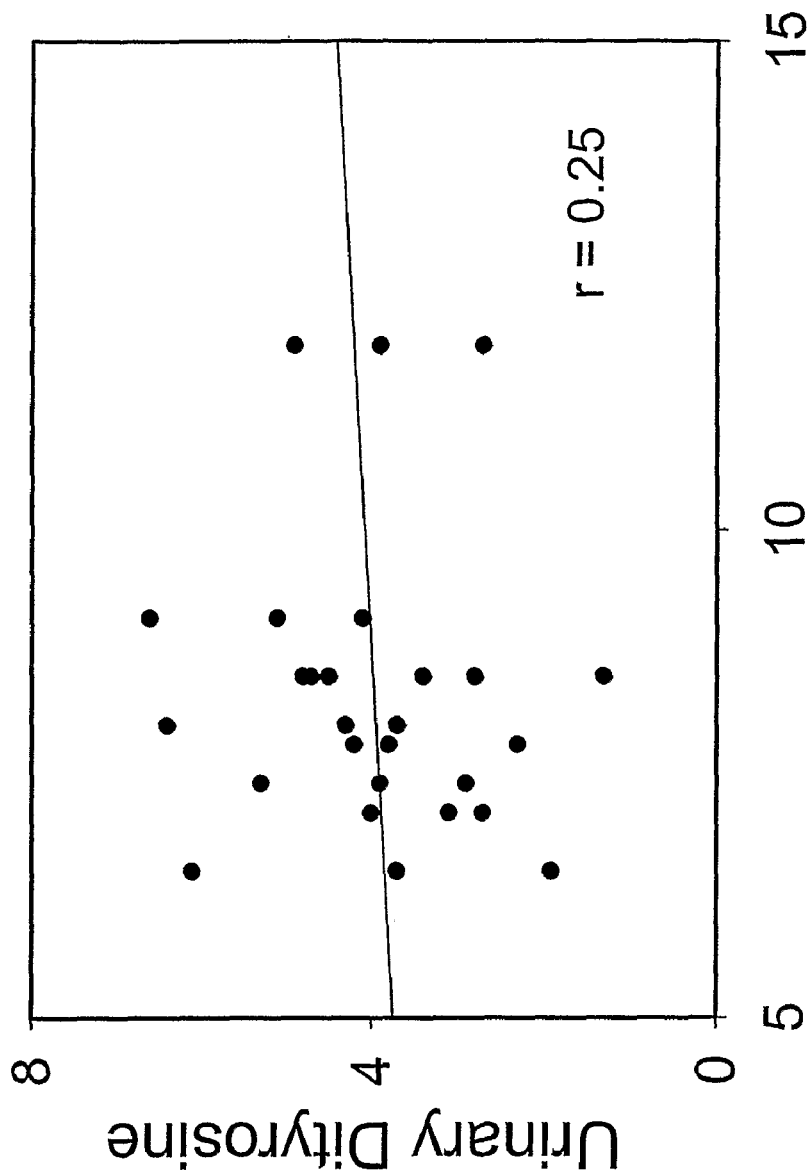
FIG. 16 depicts the correlation between dityrosine levels present in the urine in control patients and diabetic patients having undergone a renal transplant and levels of Hemoglobin A1C.
Figure 17:
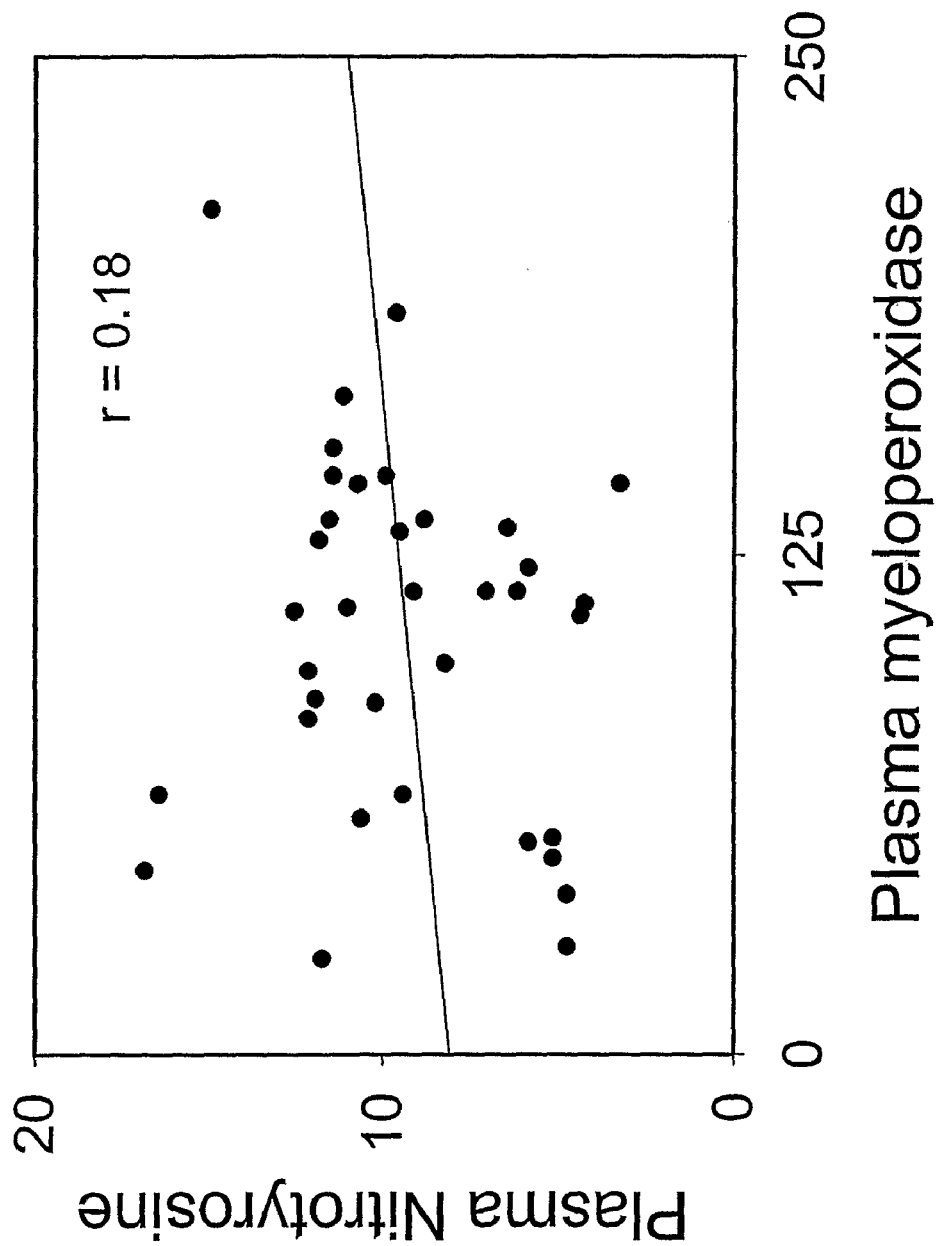
FIG. 17 depicts the correlation between nitrotyrosine levels present in the plasma in control patients and diabetic patients having undergone a renal transplant and levels of myeloperoxidase present in the plasma of the same patients.
Figure 18:
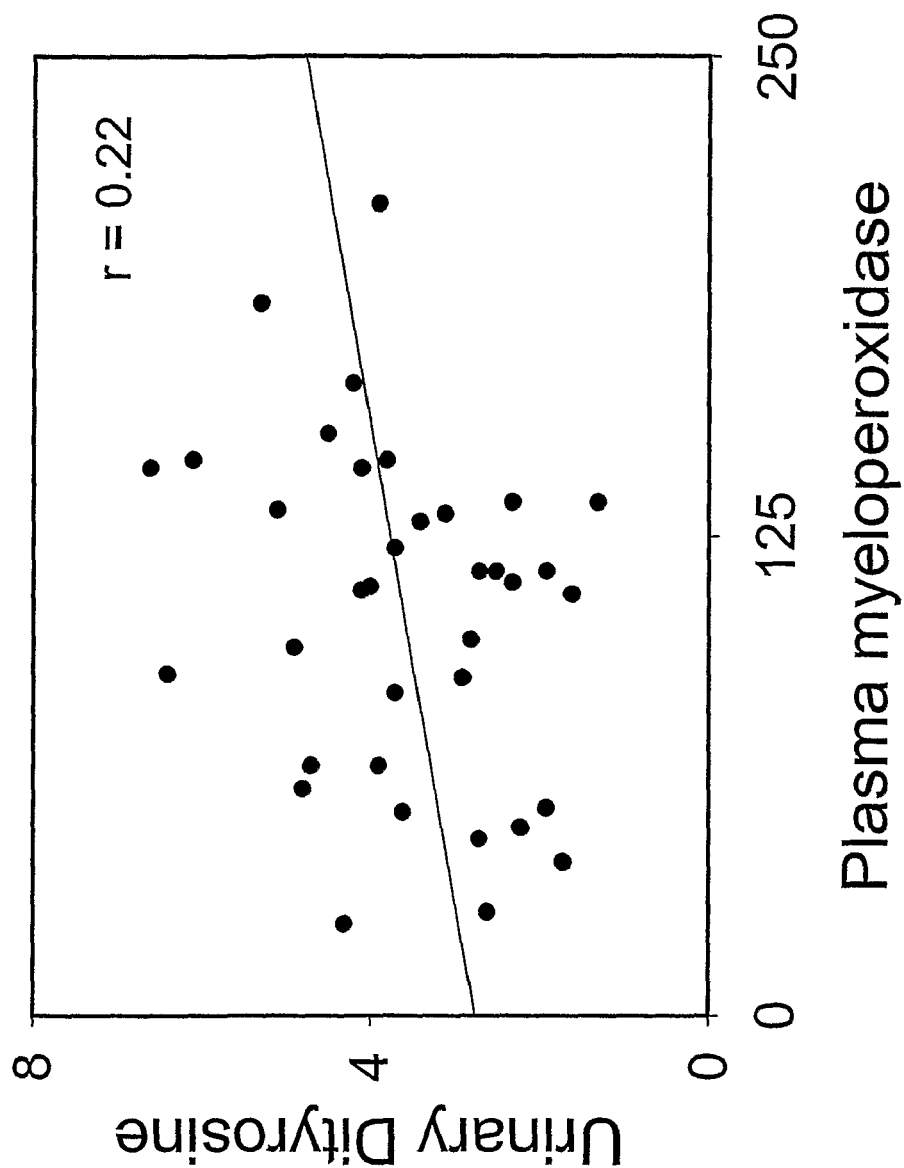
FIG. 18 depicts the correlation between nitrotyrosine levels present in the plasma in control patients and diabetic patients having undergone a renal transplant and levels of myeloperoxidase present in the plasma of the same patients.
Figure 19:
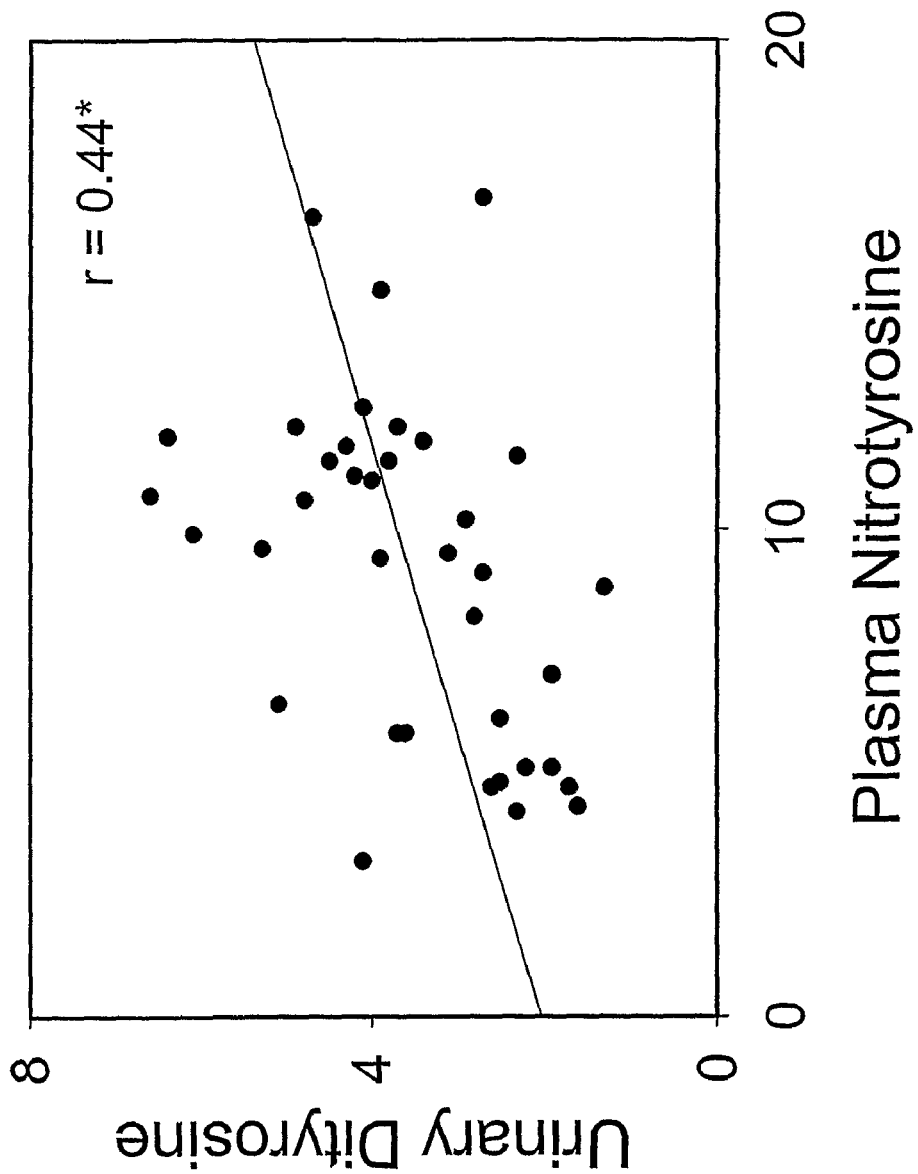
FIG. 19 depicts the correlation between dityrosine levels present in the urine in control patients and diabetic patients having undergone a renal transplant and levels of nitrotyrosine present in the plasma of the same patients.

Dityrosine levels present in the urine of diabetic patients having undergone a renal transplant are elevated in comparison to control patients as depicted in FIG. 12. Levels of circulating nitrotyrosine present in the plasma in diabetic patients having undergone a renal transplant are also elevated relative to control patients as depicted in FIG. 13. Similarly, myeloperoxidase levels present in the plasma in diabetic patients having undergone a renal transplant are elevated in comparison to control patients.

Example 4

HDL isolated from carotid atherosclerotic tissue in diabetic patients contains 3-nitrotyrosine and 3-chlorotyrosine in amounts greater than found in HDL isolated from the plasma of control patients. We quantified 3-nitrotyrosine and 3-chlorotyrosine in HDL isolated from atherosclerotic tissue obtained from diabetic patients and from the plasma of non-diabetic patient groups described in Example 3. The quantification was performed according to the methods set forth in Example 1. We isolated the HDL by sequential ultracentrifugation from atherosclerotic tissue that was freshly harvested from patients. To prevent artifactual oxidation of lipoproteins, we used buffers containing high concentrations of DTPA (a metal chelator) and BHT (a lipid soluble antioxidant). Western blotting with a monospecific rabbit antibody confirmed that lesion HDL contained a high concentration of apo A-I and a range of apparently larger immunoreactive proteins. Quantitative Western blotting demonstrated that apo A-I accounted for >50% of the protein in the HDL.

To quantify 3-nitrotyrosine and 3-chlorotyrosine, isolated HDL was delipidated, hydrolyzed, and the amino acids in the hydrolysate isolated by solid-phase extraction on a C18 column. The reisolated amino acids were derivatized and analyzed by GC/MS with selected ion monitoring in the negative-ion chemical ionization mode. The derivatized amino acids isolated from the HDL obtained from carotid atherosclerotic tissue contained compounds that exhibited the major ions identical to that of 3-nitrotyrosine and 3-chlorotyrosine. Selected ion monitoring showed that these ions co-eluted with the ion derived from $^{13}$C-labeled internal standard.

Figure 20:
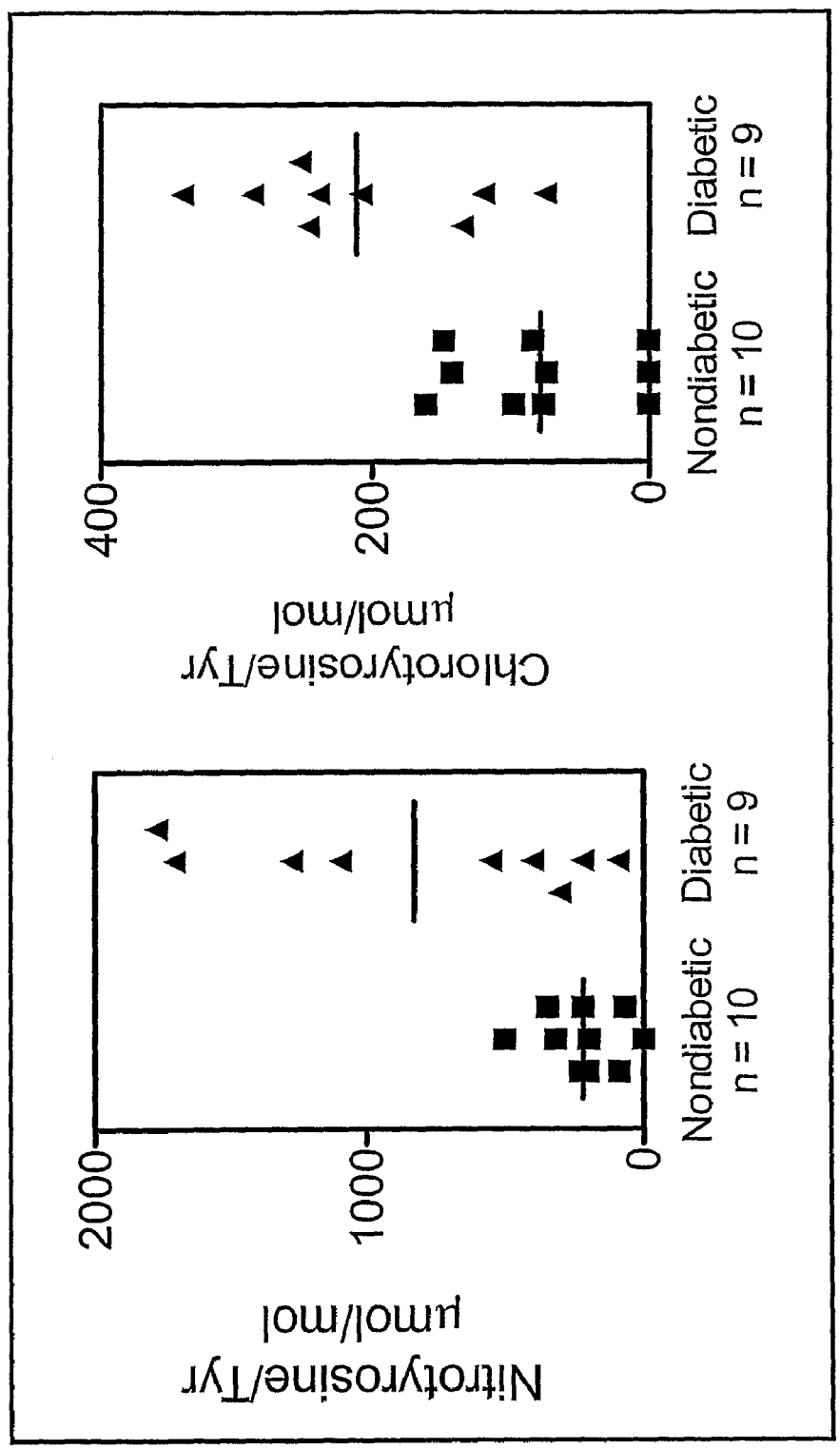
FIG. 20 demonstrates that the levels of nitrotyrosine and chlorotyrosine, respectively represented in μmol of each per mol of tyrosine, are elevated in HDL isolated from atherosclerotic tissue in diabetic patients as compared to control patients.

To assess quantitatively the contribution of nitration to the oxidation of artery wall lipoproteins, we isolated HDL from plasma of the control patients. HDL was delipidated and hydrolyzed, the resulting amino acids were isolated and derivatized, and the derivatized amino acids were quantified with isotope dilution GC/MS with selected ion monitoring. The concentration of 3-nitrotyrosine in HDL isolated from the atherosclerotic lesions of the diabetic patients was higher than that in HDL of the normal patients as depicted in FIG. 20.

What is claimed is:

1. A method for assessing the presence of cardiovascular disease wherein abnormal levels of at least one high-density lipoprotein ("HDL") oxidation product is associated with the presence of cardiovascular disease comprising the steps of:
   A) obtaining a biological sample from a subject;
   B) measuring the amount of an HDL tyrosine oxidation product in the biological sample, wherein the HDL tyrosine oxidation product is at least one of 3-nitrotyrosine, 3-chlorotyrosine or o',o'-dityrosine;
   C) comparing the amount of the HDL tyrosine oxidation product in the biological sample with a range of predetermined values indicative of a healthy population, wherein an increase in the oxidized HDL tyrosine product as compared to a predetermined normal reference range, is indicative of the presence of cardiovascular disease in the subject.

2. The method of claim 1 wherein the HDL tyrosine oxidation product is an apo A1 oxidation product.

3. The method of claim 1, wherein the cardiovascular disease is selected from the group consisting of atherosclerosis, coronary heart disease, ischemic heart disease, myocardial infarction, angina pectoris, peripheral vascular disease, cerebrovascular disease, and stroke.

4. The method of claim 1 wherein the cardiovascular disease is atherosclerosis.

5. The method of claim 1 wherein the cardiovascular disease is associated with renal disease or renal failure.

6. The method of claim 1 wherein the HDL oxidation product is 3-nitrotyrosine.

7. The method of claim 1 wherein the HDL oxidation product is 3-chlorotyrosine.

8. The method of claim 1 wherein the HDL oxidation product is o',o'-dityrosine.

9. The method of claim 1 wherein the assessing is determining risk for developing cardiovascular disease.

10. The method of claim 1 wherein the assessing is determining response of the cardiovascular disease to a treatment.

11. The method of claim 1 wherein the assessing is quantifying the severity of the cardiovascular disease.

12. The method of claim 1, wherein said one biological sample is selected from the group consisting of whole blood cells, whole blood cell lysates, erythrocytes, white blood cells, plasma, serum, urine, CSF and saliva.

13. The method of claim 1, wherein said biological sample is plasma or urine.

14. The method of claim 1, wherein measuring said HDL oxidation product is performed by immunoassay or flow cytometry.

15. The method of claim 14 wherein said measuring is performed by a method selected from the group consisting of an enzyme-linked immunosorbent assay (ELISA), a lateral flow assay, a fluorescent polarization assay, a time-resolved fluorescence assay, a microparticle capture assay, a capillary electrophoresis assay, HPLC and a fluorescence immunoassay.

16. The method of claim 1, wherein said measuring is performed by spectrophotometry.

17. A method for assessing risk for developing cardiovascular disease comprising the steps of:
   A) obtaining a biological sample from a subject;
   B) measuring the amount of at least one high-density lipoprotein ("HDL") tyrosine oxidation product in the biological sample, wherein the HDL tyrosine oxidation product is at least one of 3-nitrotyrosine, 3-chlorotyrosine or o',o'-dityrosine; and
   C) comparing the amount of the HDL tyrosine oxidation product in the biological sample with a range of predetermined values indicative of a healthy population wherein an increase in the oxidized HDL tyrosine product as compared to a predetermined normal reference range is indicative of an increased risk for developing cardiovascular disease.

18. The method of claim 17 wherein the HDL oxidation product is an apo A1 oxidation product.

19. The method of claim 17, wherein the cardiovascular disease is selected from the group consisting of atherosclerosis, coronary heart disease, ischemic heart disease, myocardial infarction, angina pectoris, peripheral vascular disease, cerebrovascular disease, and stroke.

20. The method of claim 17 wherein the cardiovascular disease is atherosclerosis.

21. The method of claim 17 wherein the cardiovascular disease is associated with renal disease or renal failure.

22. The method of claim 17, wherein the HDL tyrosine oxidation product is 3-nitrotyrosine.

23. The method of claim 17, wherein the HDL tyrosine oxidation product is 3-chlorotyrosine.

24. The method of claim 17, wherein the HDL tyrosine oxidation product is o',o'-dityrosine.

* * * * *